(12) United States Patent
Pressacco et al.

(10) Patent No.: US 10,195,039 B2
(45) Date of Patent: *Feb. 5, 2019

(54) ELBOW REPLACEMENT APPARATUS AND METHODS

(71) Applicant: LIMACORPORATE SPA, Villanova di San Daniele (Udine) (IT)

(72) Inventors: Michele Pressacco, Udine (IT); Nicola Del Negro, Sutrio (IT); Andrea Fattori, Cividale del Friuli (IT); Robert N. Hotchkiss, Riverside, CT (US); Mark P. Figgie, Riverside, CT (US); Timothy M. Wright, New York, NY (US); Joseph D. Lipman, New York, NY (US); Darrick Lo, Brooklyn, NY (US)

(73) Assignees: LIMACORPORATE SPA, Villanova di San Daniele (Udine) (IT); NEW YORK SOCIETY FOR THE RUPTURED AND CRIPPLED MAINTAINING THE HOSPITAL FOR SCPECIAL SURGERY, New York, NY (US)

( * ) Notice: Subject to any disclaimer, the term of this patent is extended or adjusted under 35 U.S.C. 154(b) by 24 days.

This patent is subject to a terminal disclaimer.

(21) Appl. No.: 15/174,617

(22) Filed: Jun. 6, 2016

(65) Prior Publication Data

US 2016/0338839 A1 Nov. 24, 2016

Related U.S. Application Data

(63) Continuation-in-part of application No. 14/081,592, filed on Nov. 15, 2013, now Pat. No. 9,358,116,
(Continued)

(51) Int. Cl.
*A61F 2/38* (2006.01)
*A61F 2/30* (2006.01)
(Continued)

(52) U.S. Cl.
CPC ............ *A61F 2/3804* (2013.01); *A61F 2/384* (2013.01); *A61F 2/385* (2013.01);
(Continued)

(58) Field of Classification Search
CPC ............ A61F 2/3804; A61F 2002/3831; A61F 2002/3813; A61F 2002/30286; A61F 2002/3822; A61F 2/384; A61F 2/385
See application file for complete search history.

(56) References Cited

U.S. PATENT DOCUMENTS 3,886,600 A * 6/1975 Kahn .................. A61F 2/30907
128/DIG. 21
3,909,854 A 10/1975 Martinez
(Continued)

FOREIGN PATENT DOCUMENTS

| CH | 664686 | 3/1988 |
|----|--------|--------|
| DE | 24 47 772 | 4/1975 |
| EP | 1 886 646 | 2/2008 |

OTHER PUBLICATIONS

"Discovery Elbow System, Surgical Technique" Biomet Orthopedics, 2008.

*Primary Examiner* — David H Willse
*Assistant Examiner* — Javier Blanco
(74) *Attorney, Agent, or Firm* — Leason Ellis LLP

(57) ABSTRACT

Apparatus and methods for total elbow replacement are provided to allow a surgeon to intraoperatively select a linked or unlinked constraint by utilizing a connection located on the body of the ulnar and/or humeral stem. Additional modularity also allows the selection of a
(Continued)

cemented or cementless stem as described herein. The modularity and adjustability provides a number of advantages.

31 Claims, 30 Drawing Sheets

Related U.S. Application Data which is a continuation of application No. 12/947,506, filed on Nov. 16, 2010, now Pat. No. 8,613,774.

(60) Provisional application No. 61/261,575, filed on Nov. 16, 2009.

(51) Int. Cl.
| | | |
|---|---|---|
| B22F 7/08 | (2006.01) | |
| B22F 3/105 | (2006.01) | |
| B33Y 10/00 | (2015.01) | |
| B33Y 80/00 | (2015.01) | |
| C23C 4/134 | (2016.01) | |

(52) U.S. Cl.
CPC .......... *A61F 2002/30286* (2013.01); *A61F 2002/30345* (2013.01); *A61F 2002/30604* (2013.01); *A61F 2002/30624* (2013.01); *A61F 2002/30626* (2013.01); *A61F 2002/3813* (2013.01); *A61F 2002/3822* (2013.01); *A61F 2002/3831* (2013.01); *B22F 3/1055* (2013.01); *B22F 7/08* (2013.01); *B33Y 10/00* (2014.12); *B33Y 80/00* (2014.12); *C23C 4/134* (2016.01)

(56) References Cited

U.S. PATENT DOCUMENTS

| | | | |
|---|---|---|---|
| 3,990,117 | A | 11/1976 | Pritchard et al. |
| 3,996,624 | A | 12/1976 | Noiles |
| 4,242,758 | A | 1/1981 | Amis et al. |
| 4,383,337 | A | 5/1983 | Volz et al. |
| 4,822,364 | A | 4/1989 | Inglis |
| 5,609,643 | A | 3/1997 | Colleran et al. |
| 5,954,770 | A | 9/1999 | Schmotzer |
| 6,027,534 | A | 2/2000 | Wack et al. |
| 6,379,387 | B1 | 4/2002 | Tornier |
| 6,699,290 | B1 | 3/2004 | Wack et al. |
| 6,716,248 | B2 * | 4/2004 | Huene .................. A61F 2/3845 623/20.11 |
| 6,890,357 | B2 | 5/2005 | Tornier |
| 7,247,170 | B2 | 7/2007 | Graham et al. |
| 7,449,028 | B2 | 11/2008 | Ball |
| 2003/0144739 | A1 | 7/2003 | Huene |
| 2006/0100712 | A1 | 5/2006 | Ball |
| 2006/0100713 | A1 | 5/2006 | Ball |
| 2006/0111788 | A1 | 5/2006 | Ball |
| 2006/0173546 | A1 | 8/2006 | Berelsman et al. |
| 2008/0033566 | A1 | 2/2008 | Berelsman et al. |
| 2009/0312840 | A1 * | 12/2009 | Morrey ................ A61F 2/3804 623/20.11 |
| 2010/0179661 | A1 | 7/2010 | Berelsman |
| 2014/0121779 | A1 | 5/2014 | Gonzalez-Hernandez |

\* cited by examiner

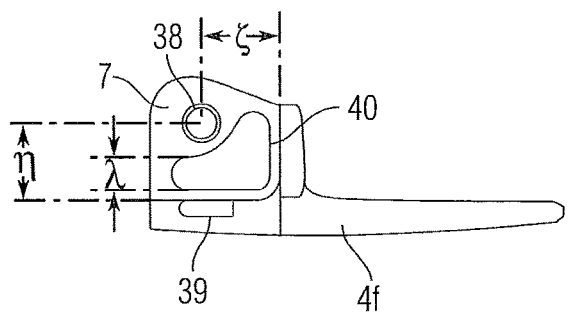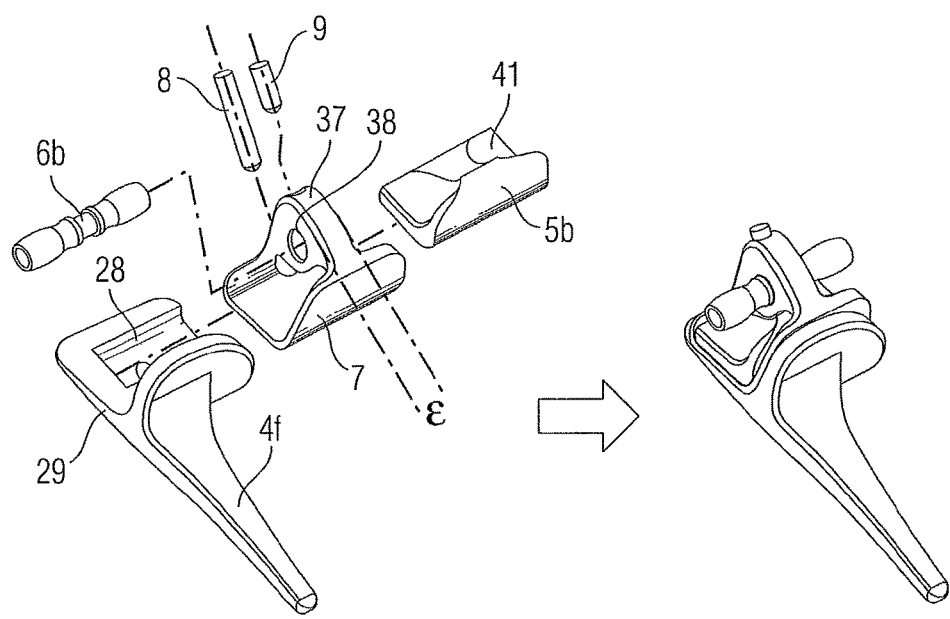
Fig. 11

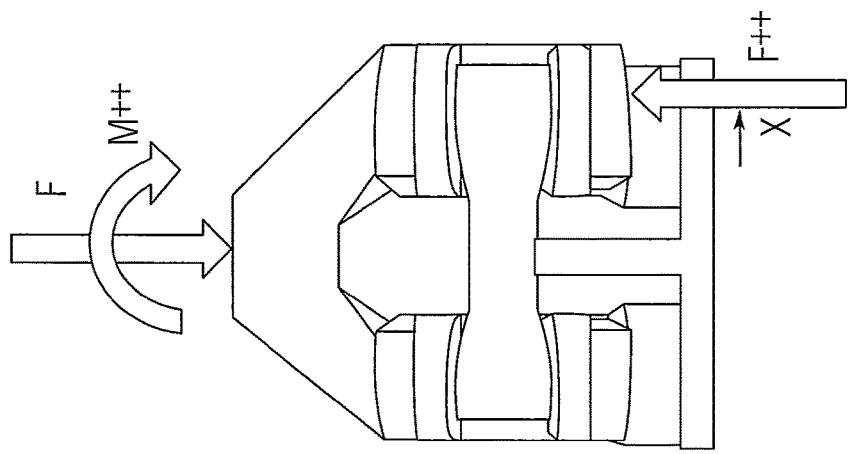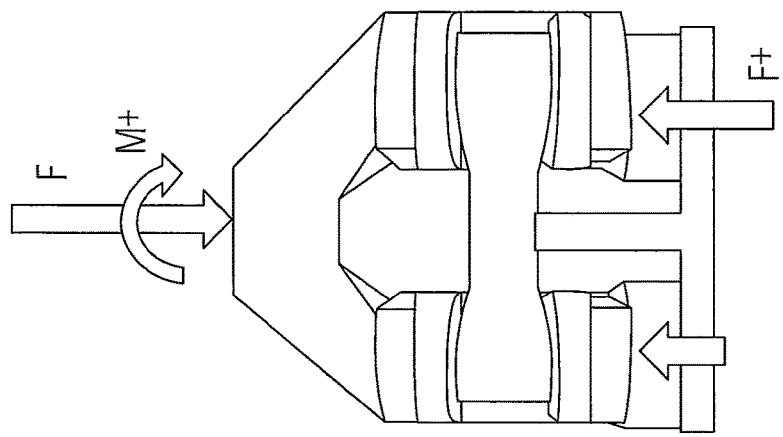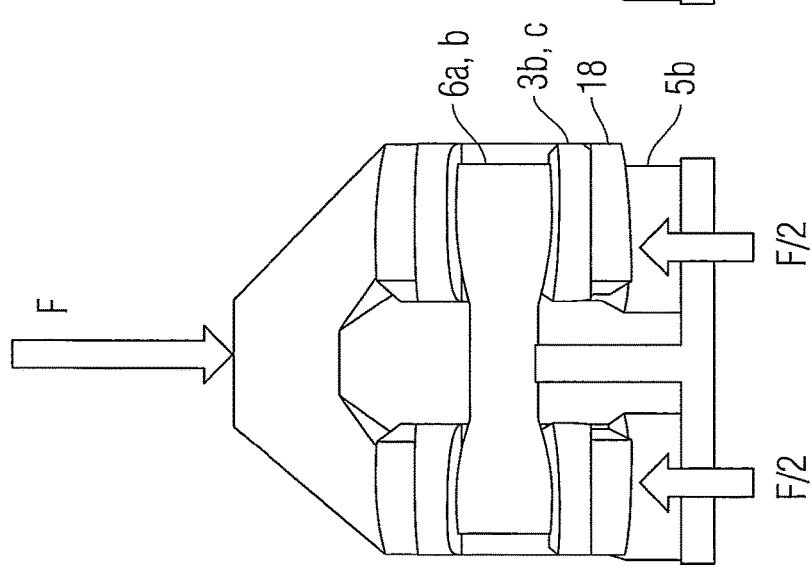
Fig. 13

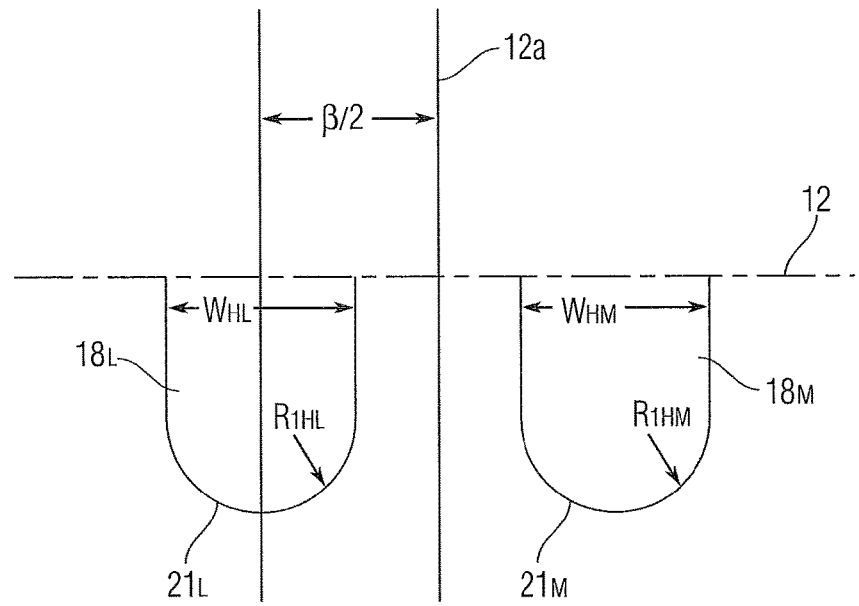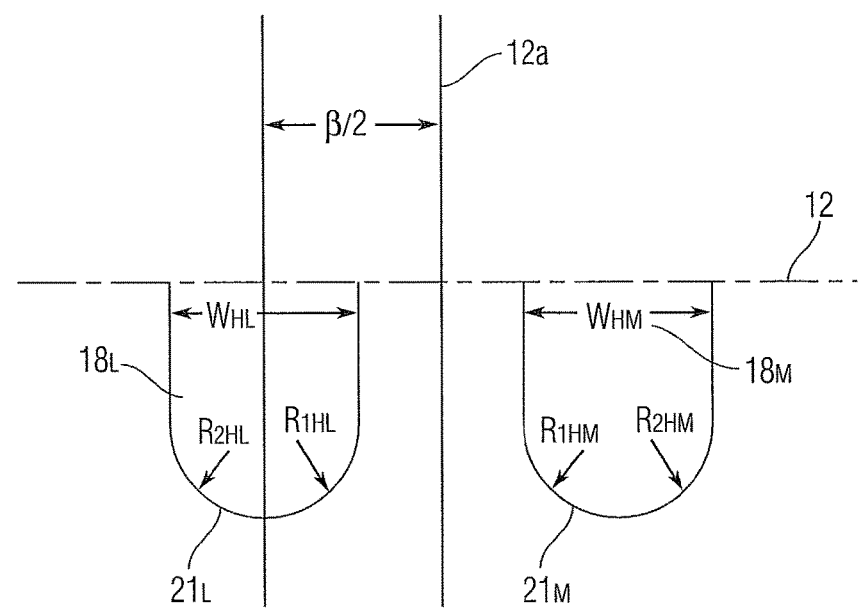
Fig. 14A

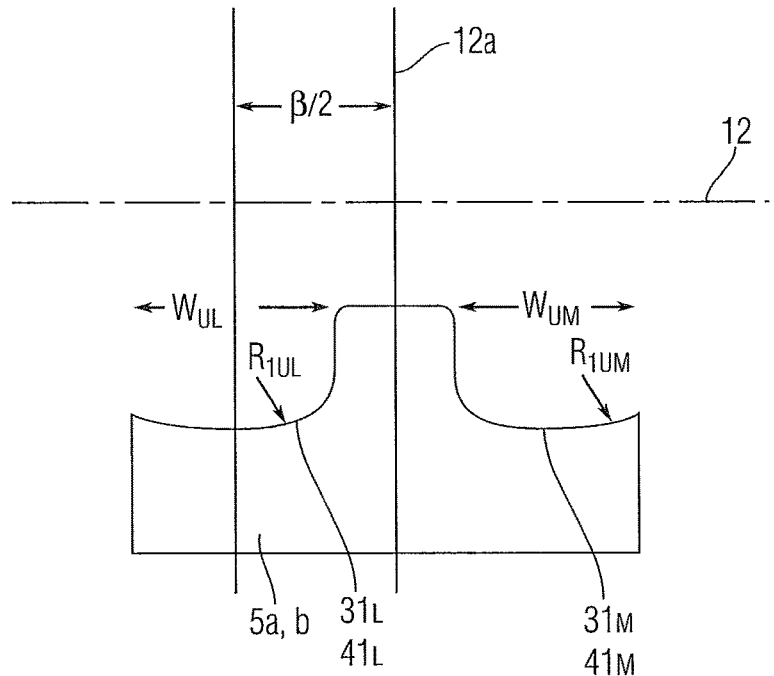
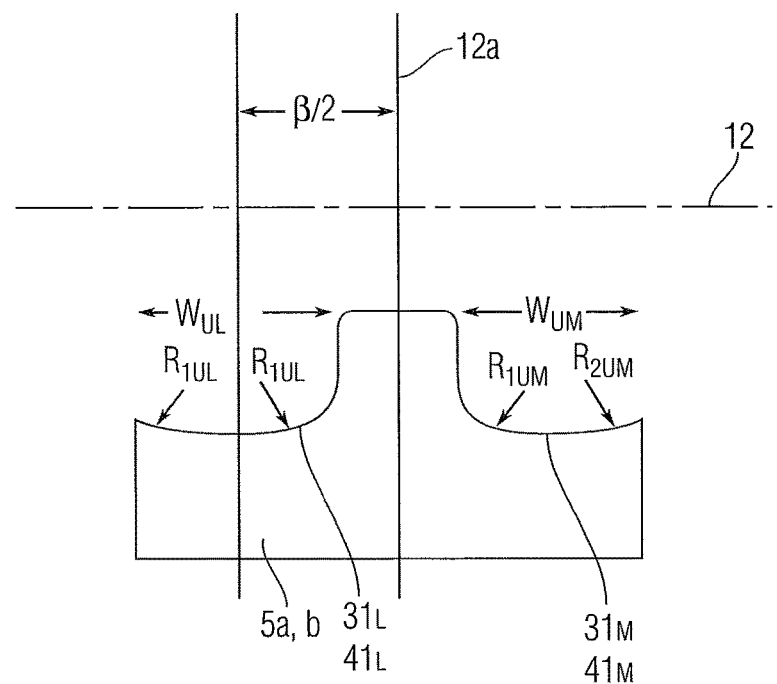
Fig. 14B

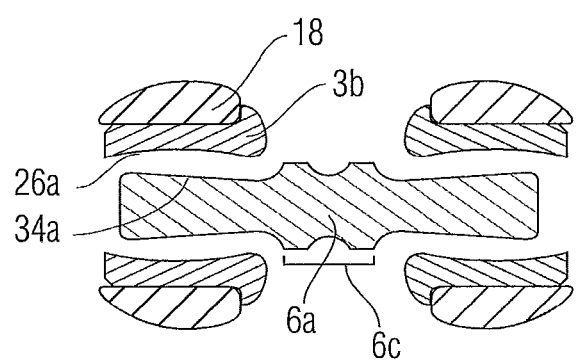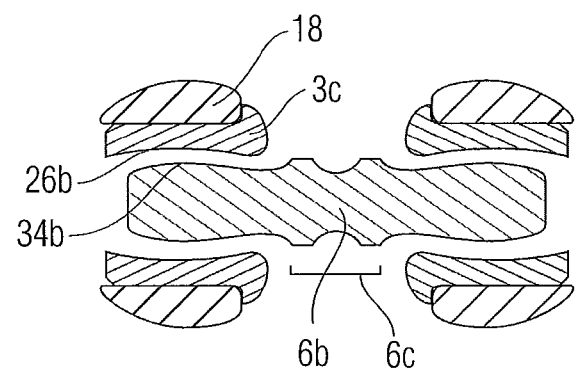
Fig. 16

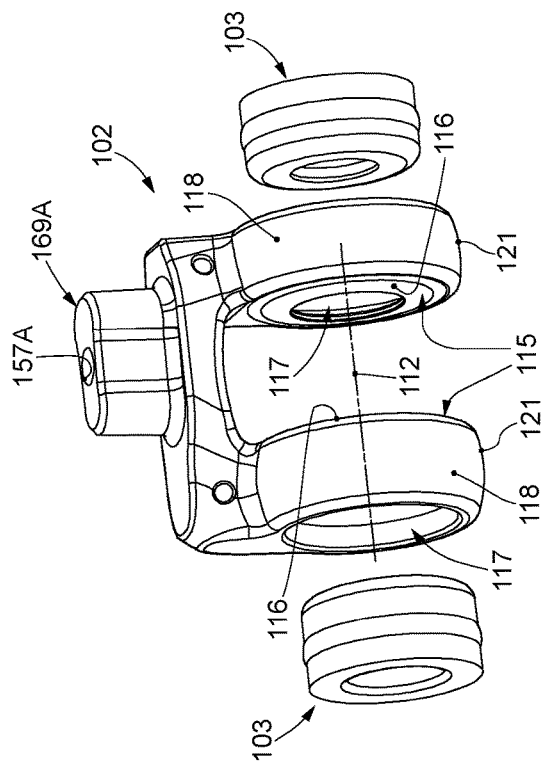
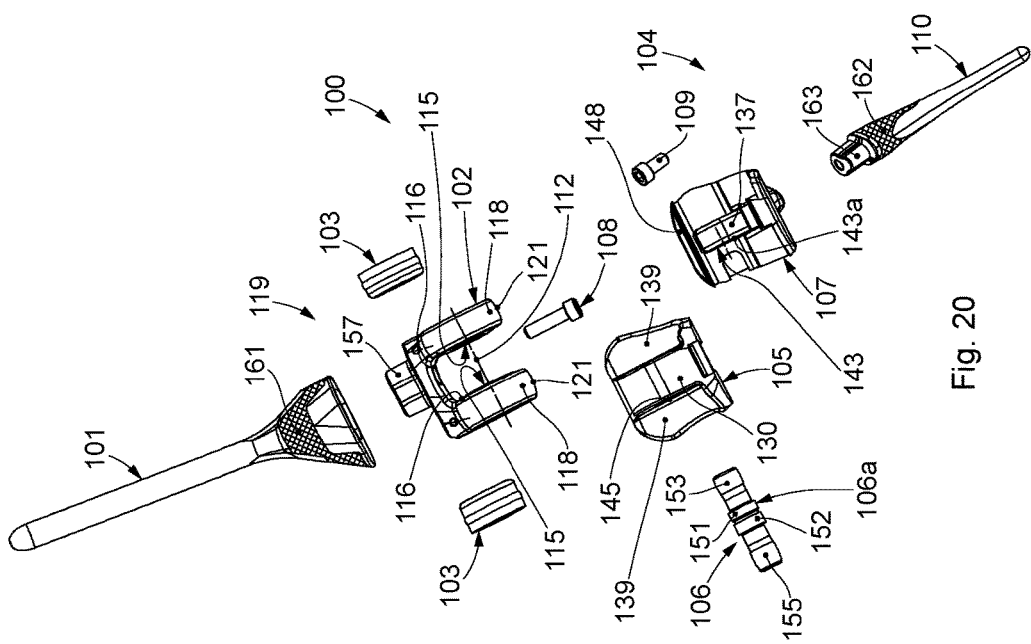

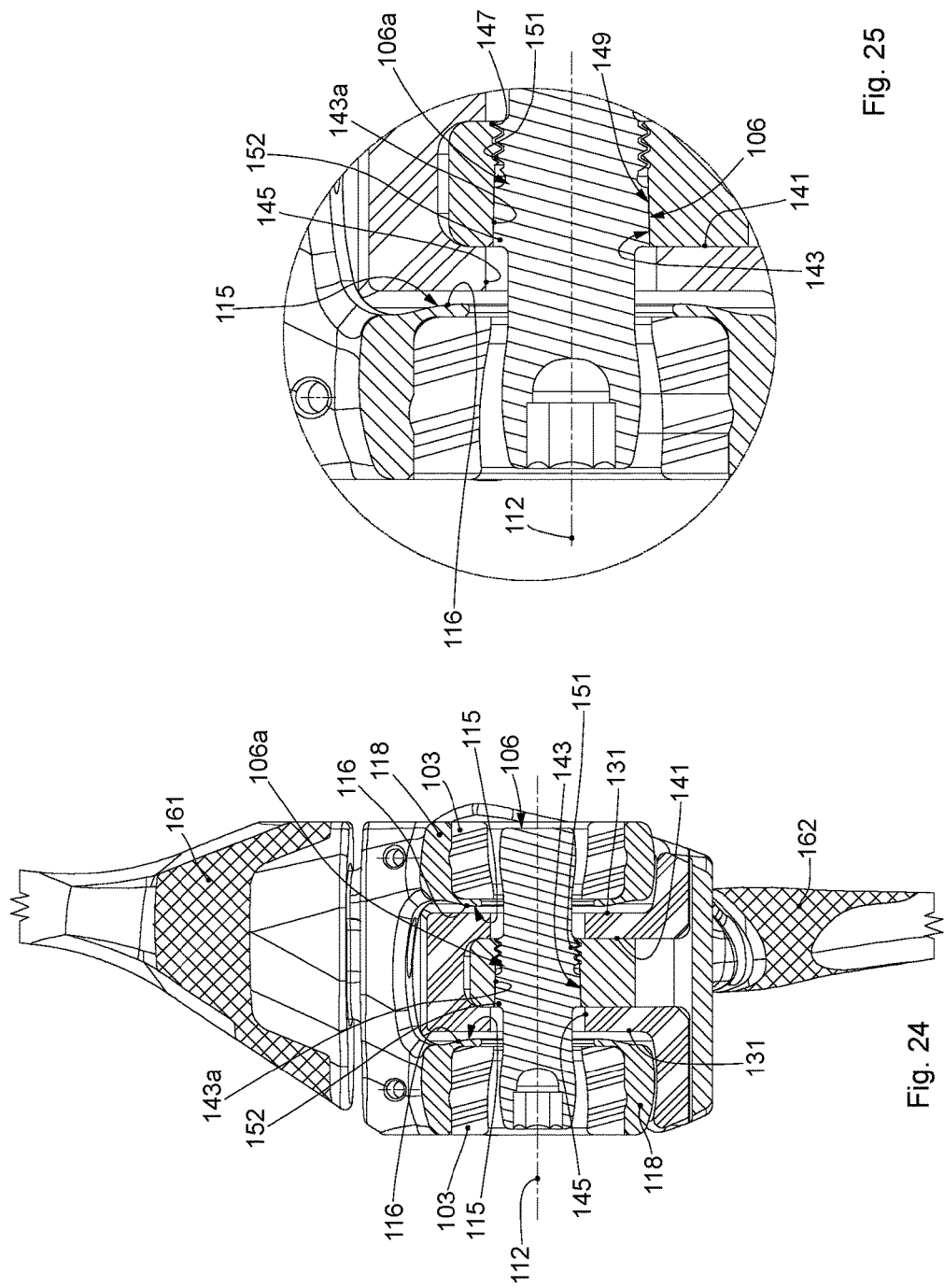

ELBOW REPLACEMENT APPARATUS AND METHODS

CROSS REFERENCE TO RELATED APPLICATION

The present application is a Continuation-in-Part of U.S. patent application Ser. No. 14/081,592 filed Nov. 15, 2013, which is a Continuation of U.S. patent application Ser. No. 12/947,506 filed Nov. 16, 2010, now U.S. Pat. No. 8,613,774, issued Dec. 24, 2013, which claims the benefit of U.S. patent application Ser. No. 61/261,575, filed Nov. 16, 2009, which is hereby incorporated by reference in its entirety.

TECHNICAL FIELD

The present invention relates to prosthetic joints and more particularly, to an elbow implant system that has an articular surface designed to gradually shift a contact point between components outwardly as the joint undergoes varus/valgus rotation and further includes a modular construction to allow for the surgeon to select different components for use depending upon the particular application and/or observations.

BACKGROUND

Joint arthroplasty is the most successful treatment thus far for relieving pain and restoring function to patients suffering from arthritis and other destructive joint problems. Hip and knee replacements are quite common with more than half a million of each procedure performed annually in the US. The popularity of hip and knee arthroplasty has been established by the efficacy and durability of these types of joint replacements. For example, the Australian national registry reports cumulative revision rates of only 4% at seven years for primary total knee arthroplasty, while the Swedish national registry reports survivorships of greater than 93% at 10 years for hip arthroplasty. For total elbow replacement, the results are not as good, with the Norwegian Arthroplasty Register reporting a failure rate of 8% and 15% at 5- and 10-year follow up, respectively.

The two leading clinical indications for total elbow arthroplasty are rheumatoid arthritis and posttraumatic arthritis. The two primary elbow replacement types used to treat these arthritic events are constrained and unconstrained designs, also referred to as linked and unlinked, respectively. Linked elbow replacements have intrinsic stability as the humeral and ulnar components are mechanically connected to one another, usually by a hinge. Some laxity exists to permit a small degree of varus-valgus and internal-external rotational movements. The humeral and ulnar components in unlinked elbow replacements, however, are not mechanically connected. For these implants, the degree of varus-valgus and internal-external rotational movements are dependent primarily on the quality of ligamentous and muscular integrity.

In the past, an unlinked elbow has been introduced with a porous coating on the fixation surfaces of the humeral and ulnar components. However, a study showed that of 32 elbow replacement arthroplasties in the test group (32 cementless humeral components, 4 cementless ulnar components), only one patient showed a radiolucent line around the humeral component after an average 3-year follow up. No radiolucent lines were exhibited around the ulnar components.

Currently, there are several devices for elbow replacement. The Coonrad-Morrey total elbow arthroplasty (TEA) system employs linked components, including polyethylene bushings on the humeral and ulnar components through which a metal axle passes, and an anterior flange on the humeral component used in conjunction with bone graft to increase torsional and anteroposterior stability in vivo. The humeral and ulnar components are cemented into place. The hinge permits ±3.5° of varus-valgus motion, with the intent that the load will be transferred to the soft tissues before max angulation is achieved.

Recent studies have evaluated the success of the Coonrad-Morrey TEAs and in particular, one study evaluated 67 Coonrad-Morrey TEAs. Of these, 37 were primary arthroplasties with a five-year survival rate of 72%. The remaining 30 were revision arthroplasties, which had a five-year survivorship of 64%. Other studies have reported ten-year survival of 51% and fifteen-year survival of 24%. Clinical results have only rivaled hip and knee replacement in less active patients, such as those with rheumatoid arthritis. For this group, implant survivorship is about 90% at five to ten years.

An implant-related failure mode with the Coonrad-Morrey TEA is wear and deformation of the polyethylene bushings, causing both decreased function of the joint as the bushing-axle constraint decreases and osteolysis secondary to the release of large volumes of polyethylene wear particles. Studies have reported radiographic evidence of bushing wear in three of six patients after less than five years, requiring patients to undergo revision surgery. Similarly, another study reported bushing wear as the cause of failure in ten patients, all of whom required revision surgery an average of five years postoperatively. A study has shown that 1% of their patients required revision surgery for an isolated bushing exchange at an average of eight years after their TEA. In yet another study, components retrieved from sixteen elbows in fourteen patients were examined and found that damage to the humeral and ulnar polyethylene bushings was nearly universal with asymmetrical thinning and elliptical plastic deformation. Metallic wear on the fixation stem of the ulnar component, consistent with loosening at the implant-cement interface, was observed in most of the cases, underscoring the additional problem of aseptic loosening in TEAs.

The Discovery Elbow System from Biomet, Inc. is a linked, cemented total elbow replacement. The hinge has an hourglass shape to maximize articular surface contact between the humeral and ulnar components. Minimal bone resection maintains the integrity of the humeral epicondyles. The device preserves the ulnar collateral ligament.

The Latitude Total Elbow Prosthesis from Tornier is a modular, cemented total elbow replacement. This device is designed to restore the normal kinematics of the elbow joint creating a modular spool that allows the surgeon to adjust the central, posterior, and anterior offset of the joint axis. A second articular component can be attached to the ulnar component to convert from unlined to linked. The device also has an optional radial component. Limitations of using the Latitude include the complete dissection of the distal humerus that is required for implantation of the components, the use of multiple jigs to locate the natural joint axis that may not be present in a patient with rheumatoid arthritis, limited triceps split to gain access to the ulnar canal, and the use of cemented components.

However, none of these devices allow for intraoperative adjustment of soft tissue tension. For the unlinked condition, conventional devices do not provide for mechanical constraint to varus/valgus motion. It would be desirable to produce an elbow replacement with an articular surface designed to gradually shift the contact point outwardly as more varus/valgus motion is initiated, thus increasing the restoring moment at the joint. It would also be desirable to provide apparatus and methods for total elbow replacement that allow a surgeon to intraoperatively select a linked or unlinked constraint, accommodate cemented or cementless fixation, as well as adjust soft tissue tension of the joint.

There is therefore a need to improve elbow replacement apparatus and methods, which overcome at least one of the drawbacks in the art. Various limitations and disadvantages of conventional solutions and technologies will become apparent to one of skill in the art after reviewing the remainder of the present application with reference to the drawings and description of the embodiments which follow, though it should be understood that this description of the related art section is not intended to serve as an admission that the described subject matter is prior art.

SUMMARY

In accordance with the present invention, apparatus and methods for total elbow replacement are provided to allow a surgeon to intraoperatively select a linked or unlinked constraint by utilizing a connection located on the body of the ulnar and/or humeral stem. Additional modularity also allows the selection of a cemented or cementless stem as described herein. The modularity and adjustability provides a number of advantages.

In one embodiment, an elbow prosthesis includes a humeral stem component having a distal end and a proximal end. The prosthesis also includes a humeral condyle (condylar) component having a distal end and a proximal end, with the proximal end of the humeral condyle component being adapted to attachably engage the distal end of the humeral stem component. The distal end of the humeral condyle component includes distally extending portions.

An ulnar stem component is provided and has a distal end and a proximal end. The ulnar stem component tapers from the proximal end to the distal end. The ulnar bearing component is adapted to attachably engage the proximal end of the ulnar stem component and the distally extending portions of the humeral condyle component.

In another embodiment, an elbow prosthesis includes a humeral stem component and an humeral condyle component associated with the humeral stem component. The humeral condyle component has distally extending portions that define condyle bearing surfaces. The prosthesis also includes an ulnar stem component and an ulnar bearing component associated with the ulnar stem component. The ulnar bearing component has bearing surfaces that receive and engage the distally extending portions of the humeral condyle component. Each of the condyle bearing surfaces and the bearing surfaces of the ulnar bearing component has a cross-section in a coronal plane that exhibits at least two different radii such that varus or valgus rotation of the humeral condyle component relative to the ulnar bearing component causes a contact point between the condyle bearing surface and the bearing surfaces of the ulnar bearing component to move outwardly (laterally).

In another embodiment, an elbow prosthesis includes a humeral implant having a stem and a humeral condyle portion disposed at an end of the stem. The humeral condyle portion includes distally extending portions. The prosthesis also includes an ulnar stem component having a distal end and a proximal end. The ulnar stem component is tapered from the proximal end to the distal end. An ulnar bearing component that is a separate component relative to the ulnar stem component is detachably coupled to the proximal end of the ulnar stem component and the distally extending portions of the humeral condyle portion. This modularity of the ulnar implant permits a common ulnar stem to be used with an ulnar bearing component that is either of a linked type or an unlinked type.

These and other aspects, features and advantages shall be apparent from the accompanying Drawings and description of certain embodiments of the invention. The drawings, which are incorporated in and constitute a part of this specification, illustrate embodiments of the present subject matter and, together with the description, serve to explain the principles of the disclosure.

The various aspects and features described in the present disclosure can be applied, individually, wherever possible. These individual aspects, for instance the aspects and features described in the attached dependent claims, can be made subject of divisional patent applications.

It is noted that anything found to be already known during the patenting process is understood not to be claimed and to be the subject of a disclaimer.

BRIEF DESCRIPTION OF THE DRAWINGS

A few exemplary embodiments of the invention are depicted in the following figures, in which:

FIG. 13 illustrates a shift in contact point at articulation as external moment is applied in accordance with some embodiments of the disclosed subject matter, FIG. 14A illustrates differences in articular geometry of the humeral condyles in accordance with some embodiments of the disclosed subject matter, FIG. 14B illustrates differences in articular geometry of the ulnar bearing surfaces in accordance with some embodiments of the disclosed subject matter.

FIG. 20 provides a perspective view of an illustrative modular elbow replacement device in accordance with some embodiments of the disclosed subject matter;

FIG. 21 provides a perspective view of a humeral condyle body of a modular elbow replacement device in accordance with some embodiments of the disclosed subject matter;

FIG. 24 provides a crosswise section of an illustrative modular elbow replacement device in accordance with some embodiments of the disclosed subject matter;

FIG. 25 provides an enlarged view of FIG. 24;

DETAILED DESCRIPTION OF EXEMPLARY EMBODIMENTS

Reference will now be made in detail to the various embodiments of the invention, one or more examples of which are illustrated in the figures. Within the following description of the drawings, the same reference numbers refer to the same components. Generally, only the differences with respect to individual embodiments are described. Each example is provided by way of explanation of the invention and is not meant as a limitation of the invention. For example, features illustrated or described as part of one embodiment can be used on or in conjunction with other embodiments to yield yet a further embodiment. It is intended that the present invention includes such modifications and variations.

Apparatus and methods for total elbow replacement as described herein allow a surgeon to intraoperatively select a linked or unlinked constraint by utilizing a connection located on the body of the ulnar and/or humeral stem. The elbow system can be either of a linked type or unliked type in that a humeral component can either be linked to an ulnar component or they can be unlinked and free of attachment. Additional modularity also allows the selection of a cemented or cementless stem as described herein.

Figure 1:
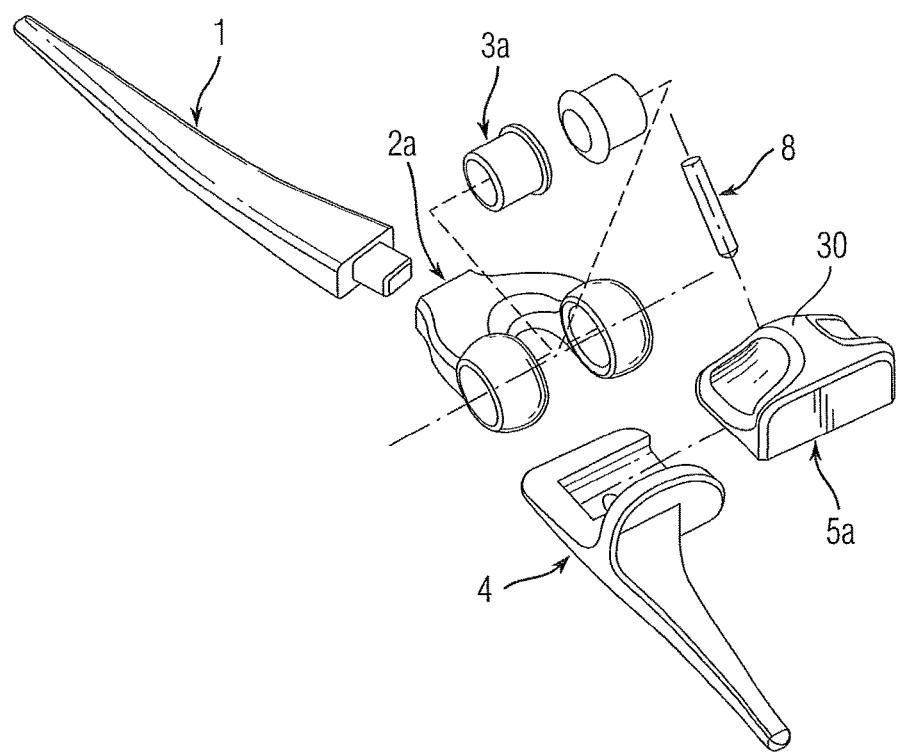
FIG. 1 provides a perspective view of an illustrative modular, unlinked elbow replacement device in accordance with some embodiments of the disclosed subject matter, FIG. 2 provides a perspective view of an illustrative modular, linked elbow replacement device in accordance with some embodiments of the disclosed subject matter, FIG. 3A provides a perspective view of an illustrative non-modular, non-cemented humeral component in accordance with some embodiments of the disclosed subject matter, FIG. 3B provides a perspective view of a non-modular, cemented humeral component in accordance with some embodiments of the disclosed subject matter, FIG. 3C provides a perspective view of a non-cemented humeral component with lateral recess in accordance with some embodiments of the disclosed subject matter, FIG. 4 provides perspective views of a non-cemented humeral sleeve in accordance with some embodiments of the disclosed subject matter, FIG. 5 provides a perspective view of a modular, humeral condyle component in accordance with some embodiments of the disclosed subject matter, FIG. 6 provides a perspective view of an alternate non-cemented, modular humeral stem design in accordance with some embodiments of the disclosed subject matter, FIG. 7 provides a perspective view of an articulation-adjustable ulnar component in linked state in accordance with some embodiments of the disclosed subject matter, FIG. 8 provides a perspective view of an alternate, non-cemented ulnar stem design in accordance with some embodiments of the disclosed subject matter, FIG. 9 provides a perspective view of an articulation-adjustable ulnar component in unlinked state in accordance with some embodiments of the disclosed subject matter, FIG. 10 provides a perspective view of an ulnar stem and unlinked ulnar bearing in accordance with some embodiments of the disclosed subject matter, FIG. 11 provides a perspective view of an ulnar stem, linked ulnar bearing, and linked ulnar bearing housing in accordance with some embodiments of the disclosed subject matter.
Figure 2:
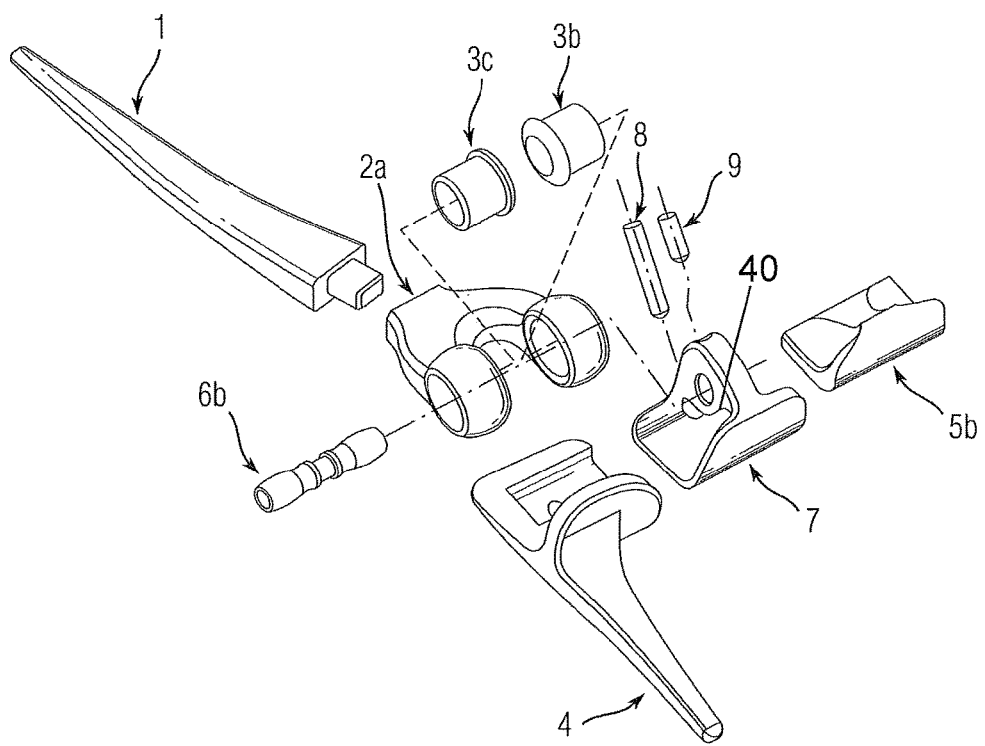

A modular total elbow replacement in accordance with some embodiments of the disclosed subject matter is shown in its unlinked and linked versions in FIGS. 1 and 2, respectively.

Non-modular, Non-cemented Humeral Component Configuration

Figure 3A:
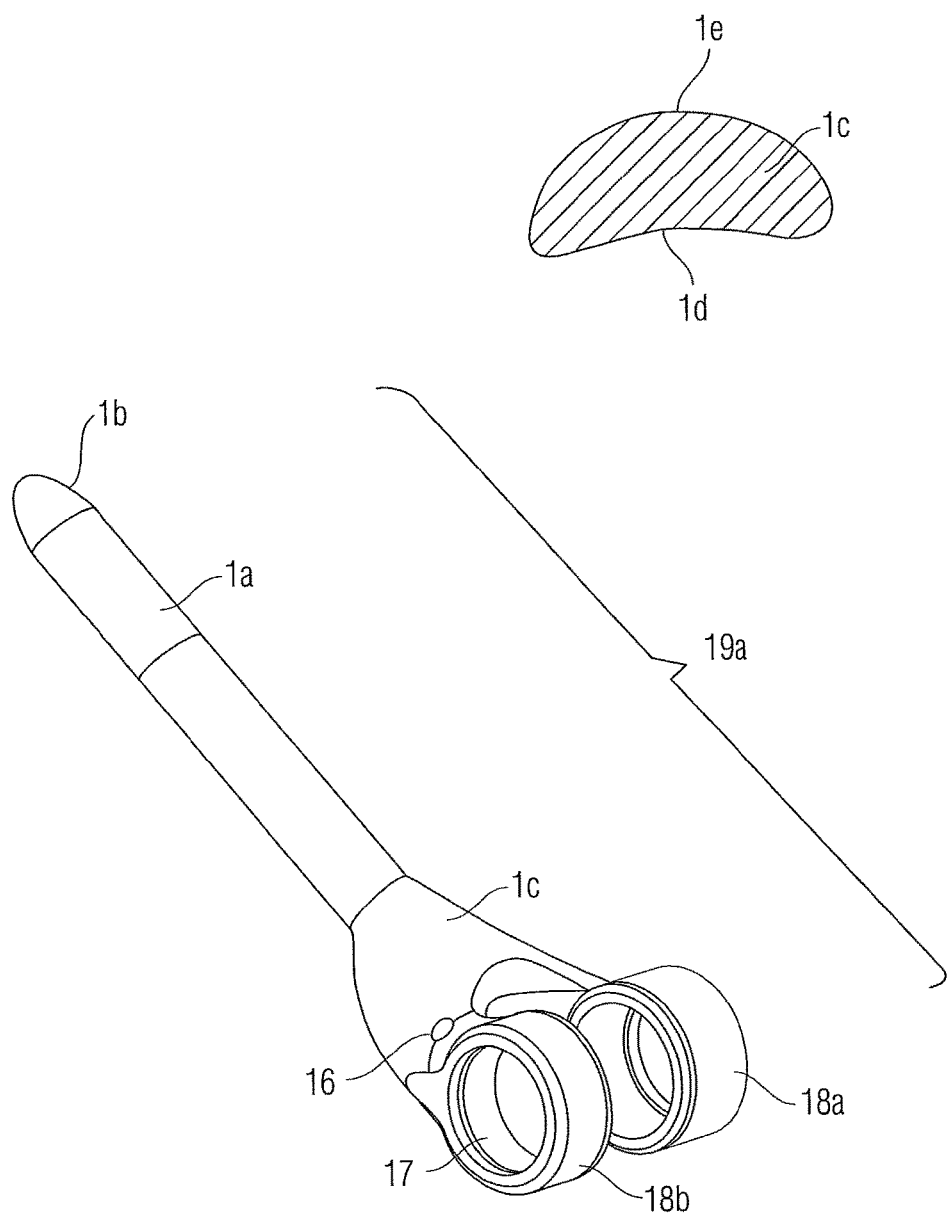
Figure 3B:
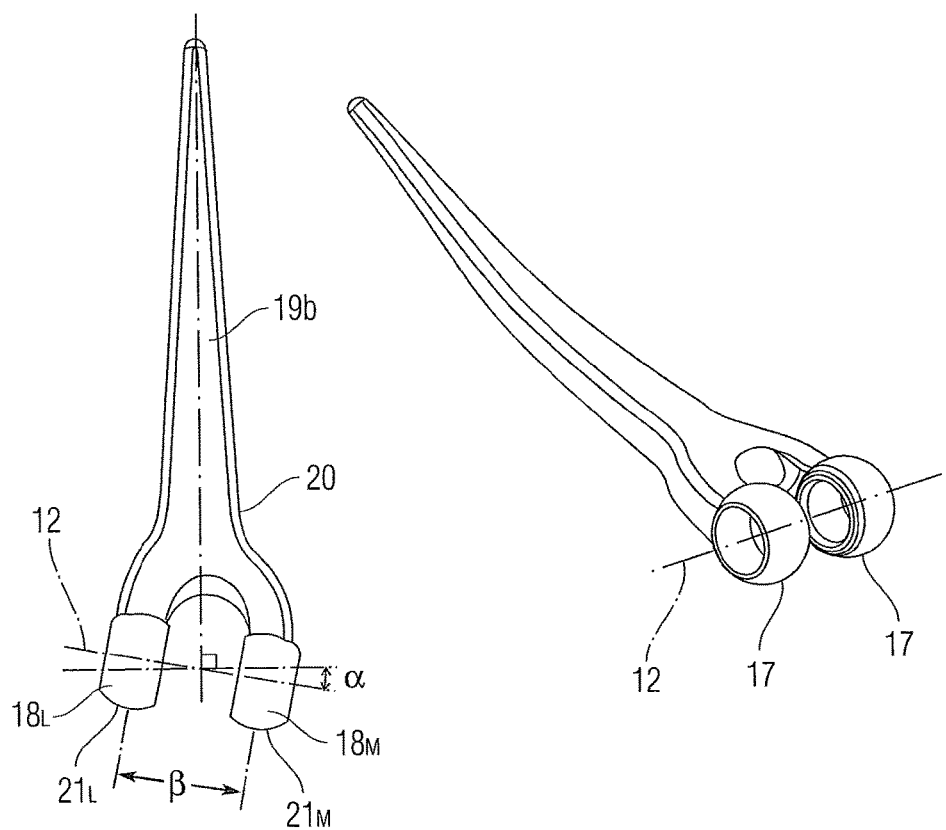

In some embodiments of the disclosed subject matter, the humeral component 19a may be non-modular and non-cemented as illustrated in FIG. 3A. In this geometry, the proximal stem 1a is a curved cylinder. The proximal end of stem 1a has a bullet shaped tip 1b to improve the distribution of load on the bone. The mid-portion geometry 1c of the humeral component 19a curves anteriorly to approximately follow normal anatomy of the humerus. The mid-portion geometry 1c has a posterior concavity 1d that interacts with olecranon fossa and an anterior convexity 1e creating a chevron-like cross-section, and is tapered medial-laterally to transfer load to the humerus as distally as possible. The outer surface of the mid-portion 1c may be coated with plasma spray or may include porous metal provided by additive manufacturing and possibly hydroxyapatite to promote cementless fixation to bone. The distal end of the humeral component 19a has two extending bodies (medial $18_M$ and lateral $18_L$ condyles) that are separated by distance β as shown in FIG. 3B. In most instances, $18_M$ will have a greater width ($W_{Mh}$) than $18_L$ ($W_{Lh}$) (FIG. 14A), improving load transfer on the medial side. The medial $18_M$ and lateral $18_L$ condyles have convex surfaces $21_{M,L}$ that contact corresponding concave unlinked ulnar bearing 5a and linked ulnar bearing 5b. The contact is non-conforming. The condyles $18_{M,L}$ each have a cylindrical hole 17 that shares an axis 12 (the implant joint axis) that may or may not be perpendicular to the long axis of the proximal end of the humeral component 19a.

Figure 3C:
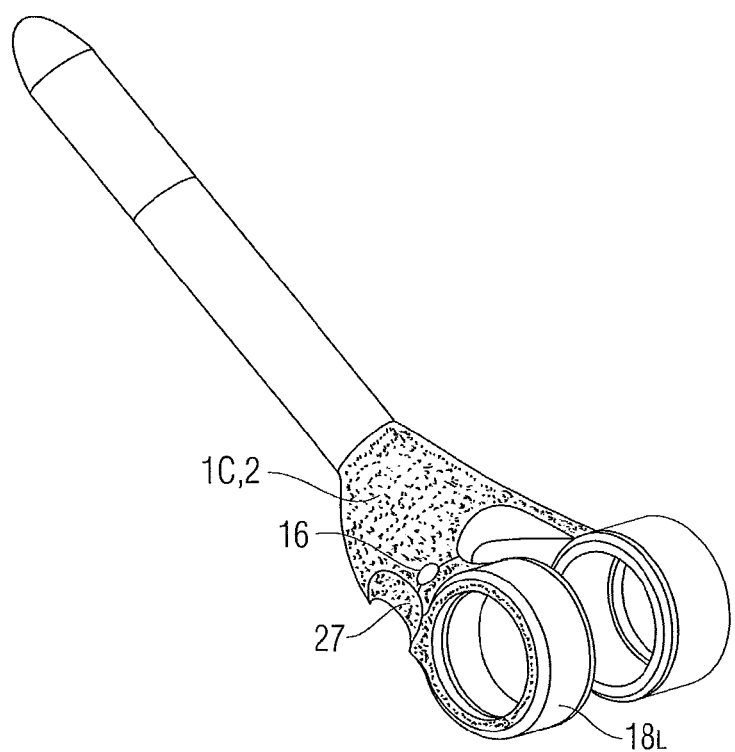

The holes 17 accept either press-fit humeral bushings 3b,c or bushing hole caps 3a. The humeral component 19 can have a built-in carry angle a as shown in FIG. 3B. The humeral component 19 can have suture holes 16 (FIGS. 3A and 3C) on the medial and lateral side for soft tissue/bone attachment. On the postero-lateral aspect of mid-portion geometry 1C adjacent to condyle $18_L$, there can be a recess 27 to contain any lateral bone fragments caused by an avulsion fracture for example. The recess 27 will protect the fixation of said fragments from shear loads when used in conjunction with sutures which pass through suture holes 16. It will be appreciated that plasma spray or porous coating around suture holes 16, recess 27, and mid-portion geometry 1c as seen in shaded regions in FIG. 3C will promote bone ingrowth.

Non-modular, Cemented Humeral Component Configuration

In some embodiments of the disclosed subject matter, the humeral component 19b, as seen in FIG. 3B, can be cemented into bone. The shape of the distal end of component 19b can be identical to component 19a. The shape of the cemented region of the humeral component 19b can be similar to embodiments shown in FIG. 3A but can be reduced in size to create room for cement (for example, ~1 to 2 mm thick cement mantle), have a rectangular or triangular cross-section for rotational stability, and have radii 20 on respective corners to reduce stress in the bone cement. There is no porous coating on the cemented component.

Humeral Sleeve

Figure 4:
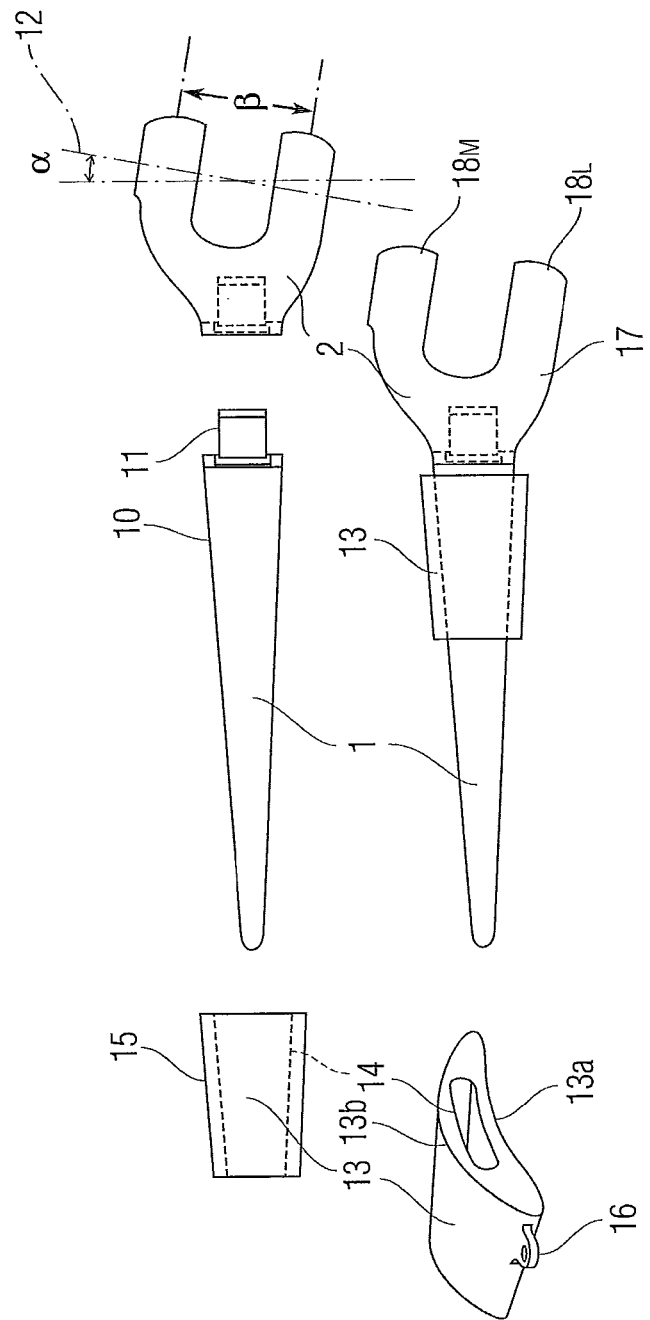

In some embodiments of the disclosed subject matter, the mid-portion geometry 1c of the humeral component 19a can be substituted with a humeral sleeve 13, as illustrated in FIG. 4. The sleeve has an inner geometry 14 that mates with the body 10. The outer surface 15 of sleeve 13 can be coated with plasma spray or may include porous metal provided by additive manufacturing and possibly hydroxyapatite to promote cementless fixation to bone. The transverse outer cross-section of the sleeve 13 has a posterior concavity 13a that interacts with olecranon fossa and an anterior convexity 13b creating a chevron to improve implant-bone contact, and is tapered medial-laterally to transfer load to the humerus as distally as possible. The elbow replacement system can include a number of humeral sleeves of different geometries such that the surgeon can select the sleeve most suited for the patient's intramedullary anatomy. Sleeve 13 can have suture holes 16 to allow a surgeon to pass sutures through the implant to attach soft tissues to the implant, thus providing additional joint stability. Sleeve 13 can be used with modular or non-modular humeral component.

Modular Humeral Component Configuration

Figure 5:
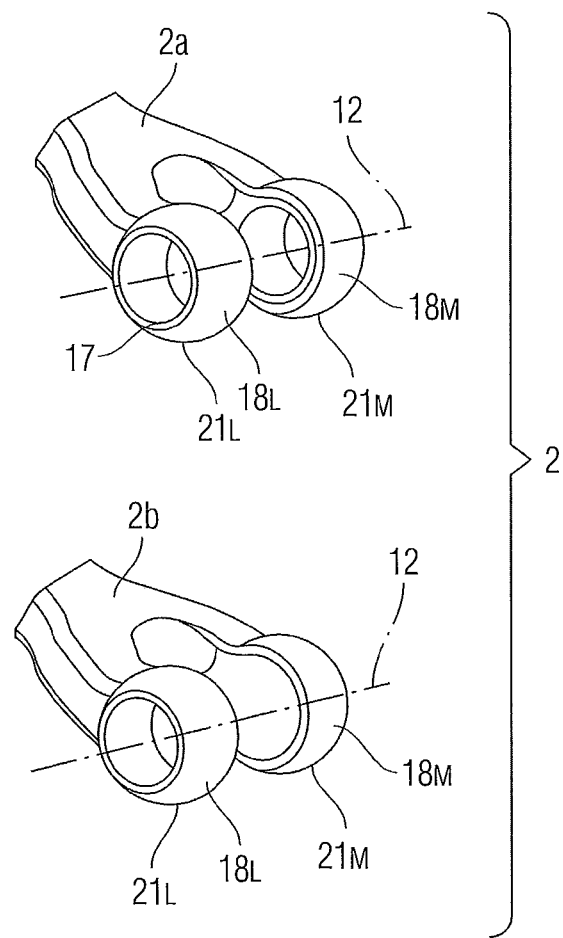

An alternative embodiment for a non-cemented and cemented humeral component design is illustrated in FIG. 4 in accordance with some embodiments of the disclosed subject matter. The humeral condyle component 2 mates with humeral extending body 11 from the humeral stem 1, thereby establishing modularity in both linked and unlinked elbow systems. The distal end of the component 2a has a geometry identical to the distal end of humeral component 19b as illustrated in FIG. 5. The unlinked elbow system can also use a humeral condyle component 2b which is identical to component 2a except that it does not have the cylindrical holes 17. Component 2 can have a built-in carry angle α.

The humeral condyle component 2 can have suture holes 16 (FIG. 3C) on the medial and lateral side for soft tissue/bone attachment. On the postero-lateral aspect of component 2 adjacent to condyle $18_L$, there can be a recess 27 to contain any lateral bone fragments. It will be appreciated that plasma spray or porous coating around suture holes 16, recess 27, and component 2 as seen in shaded regions in FIG. 3C will promote bone ingrowth.

Figure 6:
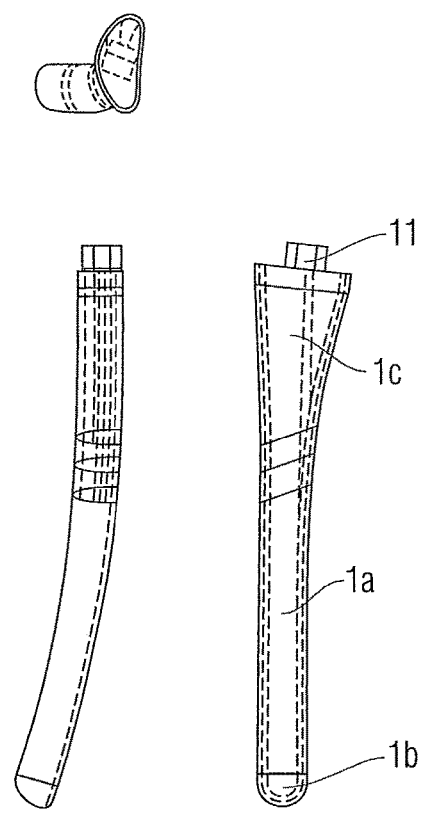

The elbow replacement system can have humeral condyle components 2 of various geometries should the surgeon want to adjust the carrying angle, the constraint, and/or the condylar geometries. The humeral stem 1 can be cementless as illustrated in FIG. 6, with a curved cylinder proximal stem 1a, bullet tip 1b, a mid-portion geometry 1c that is plasma spray coated or provided with porous metal by additive manufacturing, and a distal extending body 11 for engagement with condyle component 2. Similarly, the mid-portion geometry 1c can be substituted with humeral sleeve 13, as illustrated in FIG. 4. The humeral stem 1 can also be cemented with a rectangular or triangular cross-section for rotational stability, and have radii on respective corners to reduce stress in the bone cement. In addition, the modularity at extending body 11 permits revision without the need to remove a well-fixed humeral stem 1 from the bone canal should, for example, the condylar surfaces be worn or damaged.

The modularity of the humeral implant components thus permits a surgeon to interchange and match one humeral stem with one humeral condyle portion. Based on this feature, a hospital can predominantly stock one model of a humeral stem and a wider assortment of humeral condyle portions or vice versa. This allows greater savings by being able to stock less components as well as offering greater versatility as well as allow less components to be potentially used since an implanted stem remain in place while only the bearing component is replaced.

Articulation Adjustable Ulnar Component Configuration

Figure 7:
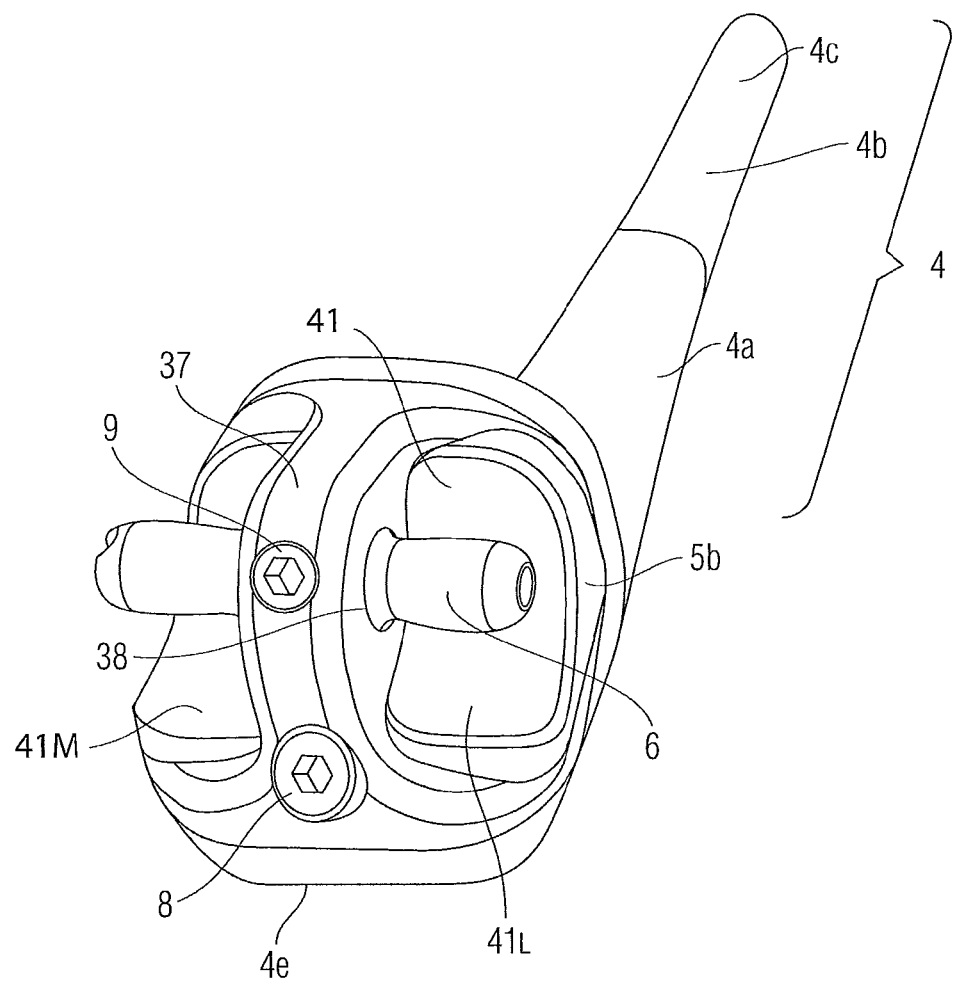
Figure 8:
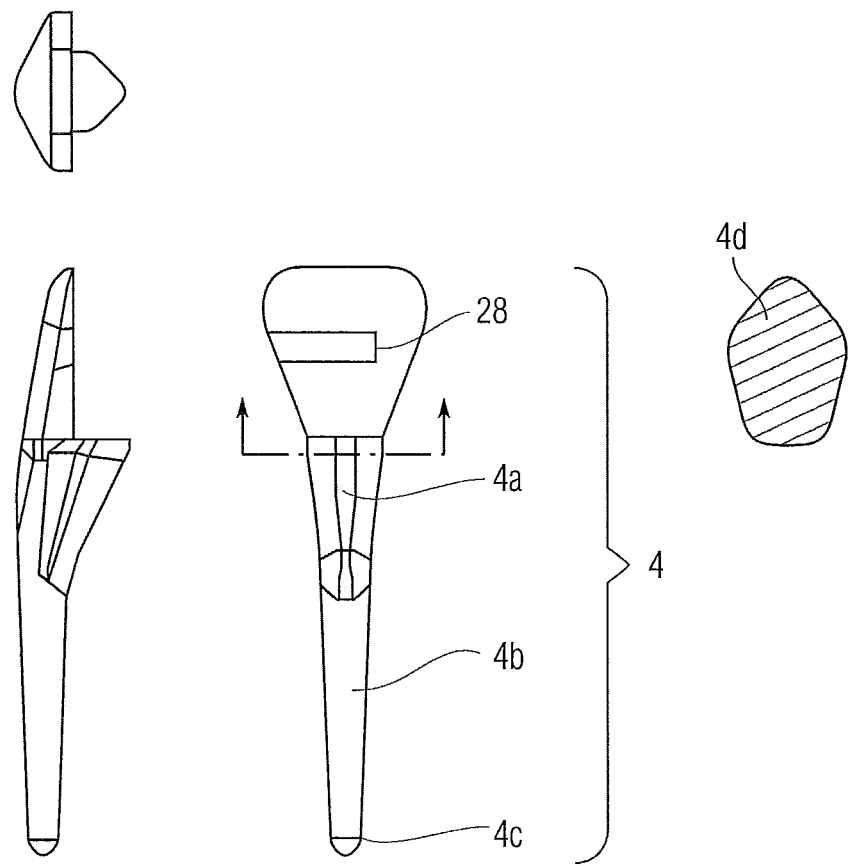

As illustrated in FIGS. 7 and 8, a non-cemented, articulation-adjustable ulnar stem 4 has a distal stem 4b that is conical in shape and terminates with a bullet shaped tip 4c to improve the distribution of load on the bone. The mid-portion body 4a has a medial/lateral and anterior/posterior and proximal/distal wedge and is approximately pentagonal in cross-section 4d where the apex interacts with the coronoid process to provide rotational stability. The proximal body has a large flat posterior surface 4e to resist additional rotational moments about the stem axis. The proximal body 29 of ulnar stem 4 has a sliding capture mechanism 28 that interacts with an unlinked ulnar bearing 5a (FIG. 1) or a linked ulnar bearing housing 7 (FIG. 2) inserted from approximately a medial and/or lateral direction establishing and adjustable articulation.

Figure 9:
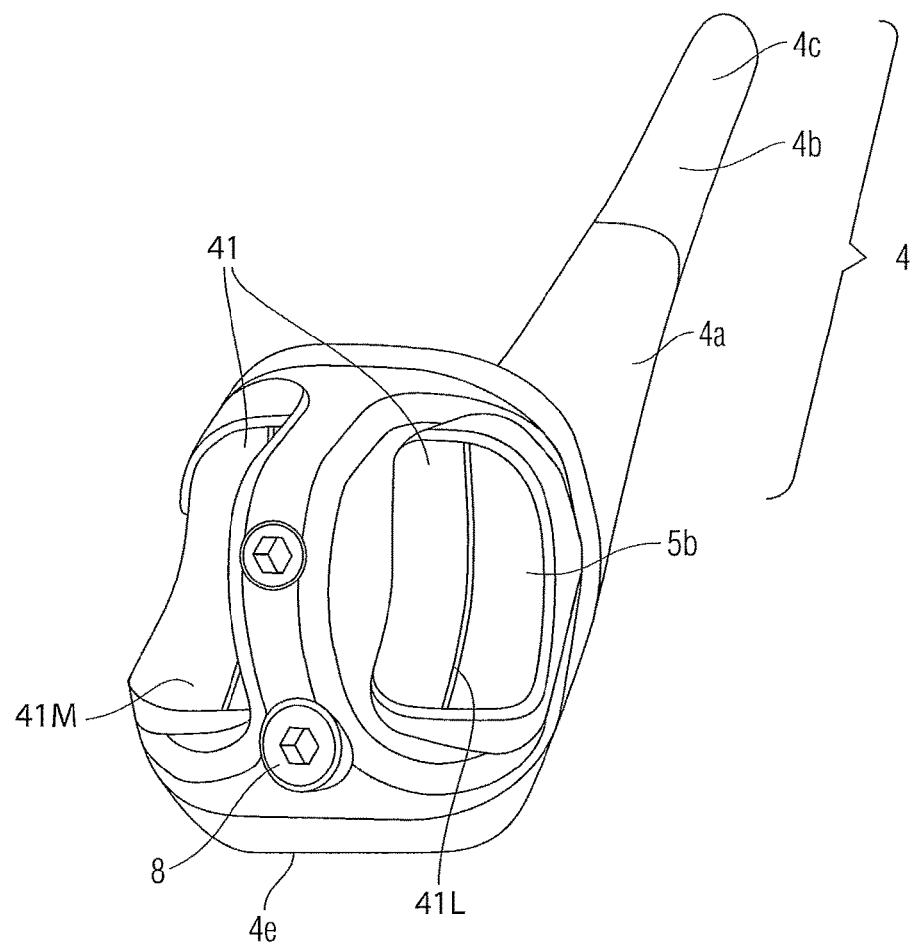

The capture mechanism 28 permits the selection of appropriately sized component, revision of worn components and/or facilitates conversion between unlinked and linked components as required. In the unlinked state as illustrated in FIG. 9, capture mechanism 28 interacts with engagement feature 33 (FIG. 10) on unlinked ulnar bearing 5a. In the linked state, capture mechanism 28 interacts with engagement feature 39 on linked ulnar bearing housing 7 (FIG. 11).

As used herein, the term ulnar bearing component at least includes an ulnar bearing that is configured to receive and engage the distally extending portions (condyles) of the humeral condlye component. As described herein, the ulnar bearing component can be of an unlinked or linked configuration. In the case of an unlinked configuration, the ulnar bearing can directly engage the ulnar stem. In the case of a linked configuration, the ulnar bearing component can include another member (housing or substrate) that supports the ulnar bearing and is adapted to engage the ulnar stem.

Unlinked Ulnar Bearing Component

Figure 10:
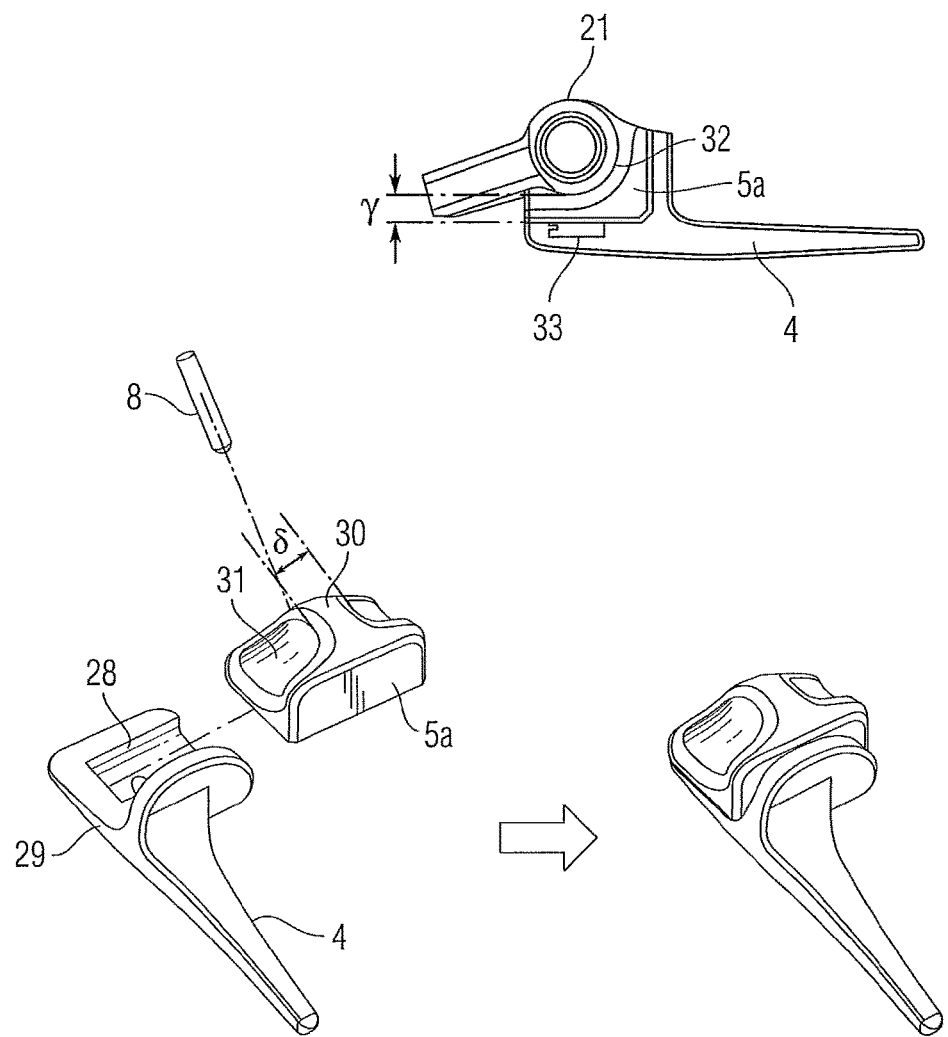

An unlinked ulnar bearing 5a, as illustrated in FIG. 10, for example, has an engagement feature 33 that interacts with the sliding capture mechanism 28 of the ulnar stem 4 and that can be inserted from approximately the medial and/or lateral direction. The bearing 5a can be rigidly locked to the stem 4 using, for example, a locking component 8. The unlinked ulnar bearing 5a has two concave surfaces $31_{M,L}$ that articulate with the convex humeral condyles $18_{M,L}$. The medial surface $31_M$ may have a greater width ($W_{Mu}$) than lateral surface $31_L$ ($W_{Lu}$) (FIG. 14B), improving load transfer on the medial side. The articulation is non-conforming. The bearing 5a also has a central post 30 that provides medial-lateral stability and a raised, distal articular face 32 to resist posterior dislocation of the ulna in flexion (FIGS. 9 and 10). The post 30 may be rectangular or trapezoidal in shape. The articulation-adjustability of ulnar stem 4 allows a surgeon to select ulnar bearings 5a of varying sizes/options defined by post thickness δ and/or bearing thickness γ for intra-operative adjustment of the degree of constraint, and/or various post alignments to adjust carry angle. The unlinked ulnar bearing 5a may be made of a low friction material, for example, ultra-high molecular weight polyethylene (UHMWPE).

Linked Ulnar Bearing Component

A linked ulnar bearing housing 7, as illustrated in FIG. 11, has an engagement feature 39 that interacts with the sliding capture mechanism 28 of the ulnar stem 4. The housing 7 has a central post 37 that provides medial-lateral stability of the linked elbow system. The housing 7 has a first opening 40 to accept a linked ulnar bearing 5b from a medial and/or lateral direction. The linked ulnar bearing 5b has two concave surfaces $41_{M,L}$ that articulate with the convex humeral condyles $18_{M,L}$. The medial surface $41_M$ may have a greater width ($W_{Mu}$) than lateral surface $41_L$ ($W_{Lu}$) (FIG. 14B), improving load transfer on the medial side. The articulation is non-conforming. The bearing 5b can either be rigidly locked to central post 37 using, for example, a locking component 8, or act as a sliding platform with respect to central post 37. Should the bearing 5b need to be replaced, it can be removed from a medial or lateral direction. The linked ulnar bearing 5b may be made of a low friction material, for example, ultra-high molecular weight polyethylene (UHMWPE). The elbow replacement system provides various housing options. The post thickness ε and/or bearing thickness λ options permit intra-operative adjustment of the degree of constraint. The post 37 has a second opening 38 for axle 6. The axle hole 38 location option allows the surgeon to adjust anterior-posterior η and/or superior-inferior offset of the joint axis 12. The axle 6 can be assembled from the medial and/or lateral direction to the central post 37 in vivo. The axle 6 can be rigidly locked to housing 7 using, for example, a locking component 9. The central portion 6c of axle that mates with housing 7 can have a D-shaped cross-section to prevent rotation about the joint axis 12. The central portion 6c may have a stop to prevent the central portion from advancing beyond central post 37. The ends 34 of the axle articulate with the inner diameters of the humeral bushings 3b,c.

The cemented ulnar stem 4f (FIG. 11) will have a similar shape to the non-cemented ulnar component 4 (FIG. 8) proximally, but may have a rectangular or triangular cross-section with rounded edges in the mid-4a and distal portion 4b and be reduced in size to create room for cement (for example, ~1 to 2 mm thick cement mantle).

Non-conforming Articulation Between Humeral and Ulnar Bearing Components

Figure 12:
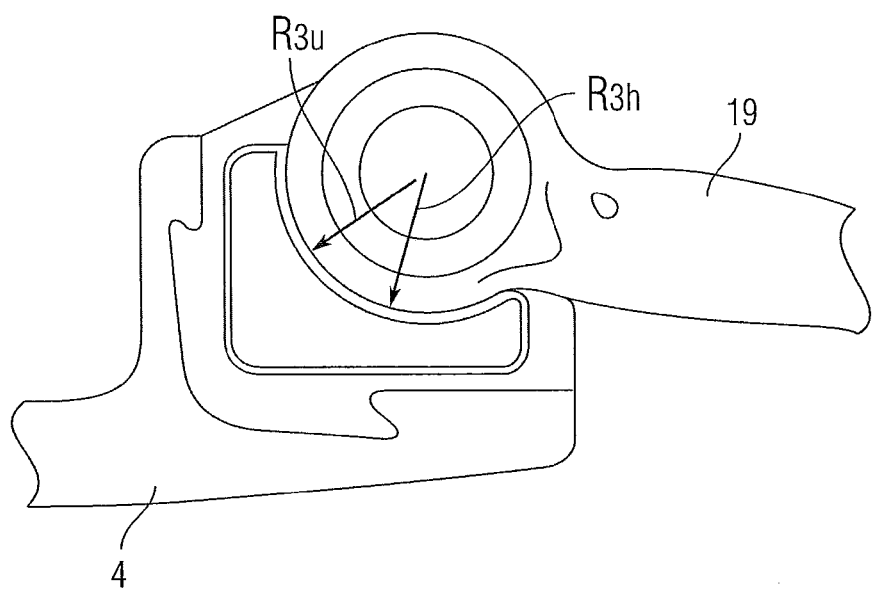
FIG. 12 illustrates differences in articular geometry between the humeral condyles and ulnar bearing surfaces in accordance with some embodiments of the disclosed subject matter.

The articulation between the humeral condyles $18_{M,L}$ and ulnar bearings 5a,b is not completely conforming in the sagittal plane ($R_{3h} < R_{3u}$) as illustrated in FIG. 12. The ratio of $R_{3h}/R_{3u}$ is approximately 0.95.

Figure 14C:
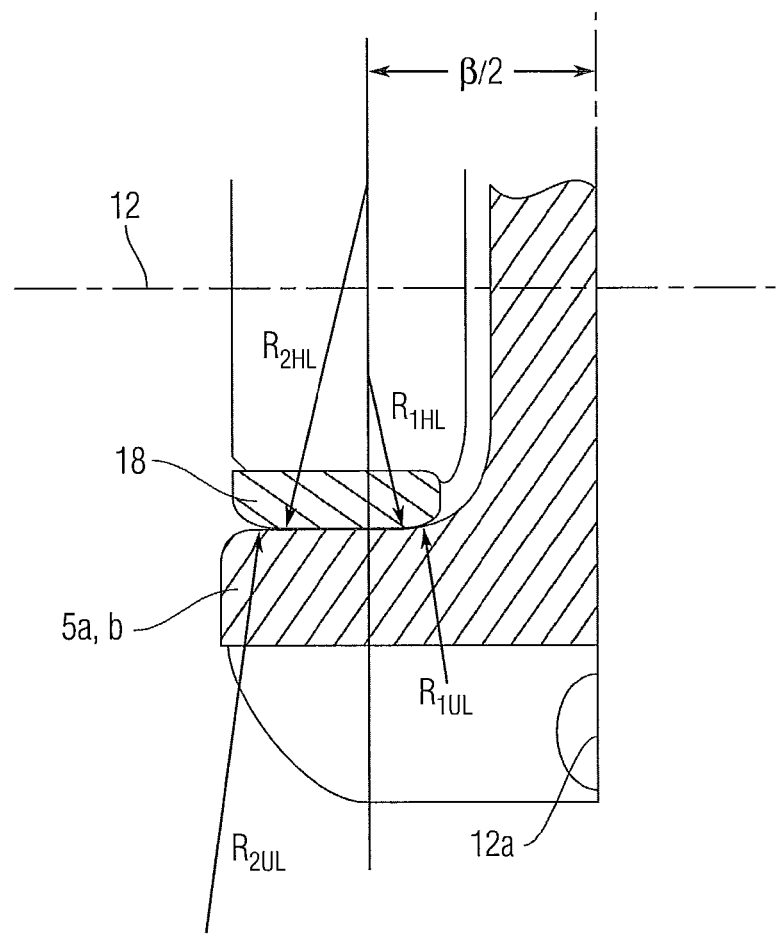
FIG. 14C illustrates the articulation between the humeral and ulnar components in accordance with some embodiments of the disclosed subject matter, FIG. 15 provides perspective views of a bushing hole cap and bushings in accordance with some embodiments of the disclosed subject matter, FIG. 16 provides a sectional view of a humeral bushing and axle in accordance with some embodiments of the disclosed subject matter, FIG. 17 provides a sectional view of an elbow joint in varus-valgus state in accordance with some embodiments of the disclosed subject matter, FIG. 18 provides sectional views illustrating articulation of the bushing hole cap and bushings of FIG. 15 in accordance with some embodiments of the disclosed subject matter, and FIG. 19 provides a perspective view of a radial head component in accordance with some embodiments of the disclosed subject matter.

The articulation between the humeral condyles $18_{M,L}$ and ulnar bearings 5a,b in the coronal plane is not completely conforming as seen in FIGS. 13 and 14C. The humeral condyle articular surfaces $21_{M,L}$ has a principal axis of rotation as defined by joint axis 12 as seen in FIGS. 14A,B,C. The articular surface $21_L$ is created by revolving a single radius $R_{1HL}$ about axis 12 creating a convex surface. Thus, in one embodiment, the articular surface $21_L$ and $21_M$ can be defined by the same radius (i.e., $R_{1HL}=R_{1HM}$) (see FIG. 14A).

An alternative embodiment of articular surface $21_L$, as illustrated in FIGS. 14A and 14C, similarly has a principal axis, but instead has two different radii $R_{1HL}$ (near midline 12a) and $R_{2HL}$ (away from midline 12a) that tangentially meet at a distance β/2 away from midline 12a. Radii $R_{1HL}$ and $R_{2HL}$ are revolved around joint axis 12 to create a convex surface. In other words, the bearing surface (articular surface $21_L$, $21_m$) of each condyle $18_{M,L}$ is defined by at least two different radii. In the figures, radius $R_{1HL}$ represents an inner (medial) radius of the lateral condyle $18_L$, while radius $R_{2HL}$ represents an outer (lateral) radius of the lateral condyle $18_L$. Similarly, radius $R_{1HM}$ represents an inner (medial) radius of the medial condyle $18_M$, while radius $R_{2HM}$ represents an outer (lateral) radius of the medial condyle $18_M$. It will therefore thus be appreciated that the radii of the condyles $18_{M,L}$ at the center of the implant are different than the radii at the outer (lateral) edges of the respective condyles (lateral edges of the implant).

The medial-lateral width of condyles $18_m$ and $18_L$ are defined by $W_{HM}$ and $W_{HL}$, respectively. The medial articular surface $21_M$ may not be equivalent to the lateral articular surface $21_L$ when the following conditions exist: radius $R_{1HM}$ does not be equal to $R_{1HL}$, radius $R_{2HM}$ does not be equal to $R_{2HL}$, and/or $W_{HM}$ does not equal $W_{HL}$.

The articular surface $31_L$, $41_L$ is created by revolving a single radius $R_{1UL}$ about axis 12 creating a concave surface (FIG. 14B). Thus, in one embodiment, the articular surface $31_L$ and $31_M$ (and $41_L$ and $41_M$) can be defined by the same radius (i.e., $R_{1UL}=R_{1UM}$) (see FIG. 14B).

An alternative embodiment of articular surface $31_L$, 41L, as illustrated in FIGS. 14B and 14C, has instead two different radii $R_{1UL}$ (near midline 12a) and $R_{2UL}$ (away from midline 12a) that are revolved around joint axis 12 to create a concave surface. In the figures, radius $R_{1UL}$ represents an inner (medial) radius of the lateral surface $31_L$, $41_L$, while radius $R_{2UL}$ represents an outer (lateral) radius of the lateral surface $31_L$, $41_L$. Similarly, radius $R_{1UM}$ represents an inner (medial) radius of the medial surface $31_M$, $41_M$, while radius $R_{2UM}$ represents an outer (lateral) radius of the medial surface $31_M$, $41_M$. It will therefore thus be appreciated that the radii of the surface $31_{M,L}$ and $41_{M,L}$ at the center of the implant are different than the radii at the outer edges of the respective condyles (lateral edges of the implant).

The medial-lateral width of surfaces $31_M$ and $41_M$ is defined by $W_{UM}$. The medial-lateral width of surfaces $31_L$ and $41_L$ is defined by $W_{UL}$. The medial articular surfaces $31_M$ and $41_M$ may not be equivalent to the lateral articular surfaces $31_M$ and $41_M$, respectively when the following conditions exist: radius $R_{1UM}$ does not be equal to $R_{1UL}$, radius $R_{2UM}$ does not be equal to $R_{2UL}$, and/or $W_{UM}$ does not equal $W_{UL}$. As the two radii humeral condyle 18 embodiment pivots about respective two radii ulnar bearing surface 31,41 with an applied external moment, as seen in FIGS. 13 and 14C, the contact location on respective articulation shifts outwardly (away from midline 12a) thereby gradually increasing the restoring moment.

The articular surfaces $31_{M,L}$ of unlinked ulnar bearing 5a are very similar to articular surfaces $41_{M,L}$. The unlinked bearing 5a, however, has a raised distal face 32, as seen in FIG. 9, and extends further superiorly than linked bearing 5b. As a result, the concavity opens up at these extending regions to increase range of motion of the elbow joint.

Accordingly, the articulation between the humeral condyles $18_{M,L}$ and ulnar bearings 5a,b in the coronal plane is not completely conforming as illustrated in FIGS. 13 and 14C. The ratios of $R_{1HL}/R_{1UL}$, $R_{1HM}/R_{1UM}$, $R_{2HL}/R_{2UL}$, and $R_{2HM}/R_{2UM}$ are approximately 0.85-0.98.

It will be understood that the top arrow in FIG. 13 describes an applied compressive force (F) across the joint, and the 2 bottom arrows describe the joint reaction force (F/2). As a varus moment (M+) (represented by the first curved arrow) is applied, the joint reaction force (F+) becomes greater on the medial side (longer bottom arrow) than the lateral side (shorter bottom arrow). As a greater varus moment (M++) (represented by the second curved arrow) is applied, the joint reaction force (F++) is completely on the medial side creating lift-off on the lateral side. In addition, the contact location of joint reaction force (F++) and shifts outwardly distance X as $R_{2HL}$ rolls onto $R_{2UL}$ as indicated in the rightmost figure of FIG. 13.

Thus, in accordance with one embodiment of the present invention, the bearing surfaces of the humeral condyles $18_{M,L}$ and ulnar bearings 5a,b are not toroidal in shape as in conventional designs but instead, each of the associated bearing surfaces has a cross-section in a coronal plane that exhibits at least two different radii. This construction provides for a shifting or migrating contact (in the lateral direction) between the two mating components during movement between the two components and provides for the advantages described herein.

Humeral Bushings for Linked Configuration

Figure 15:
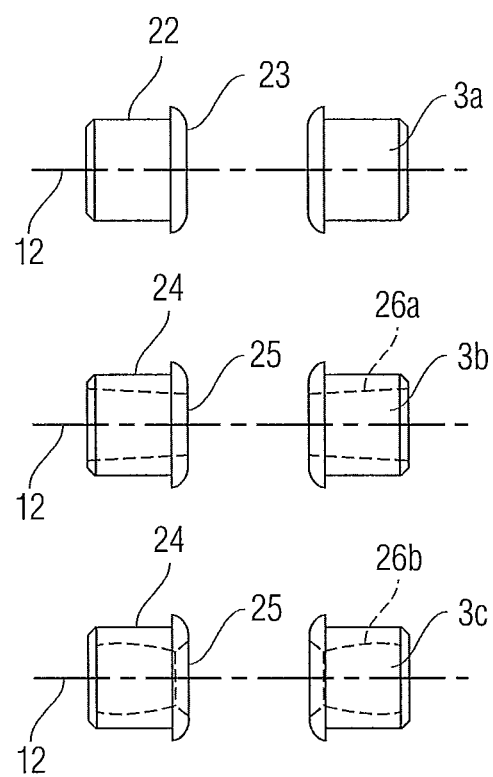
Figure 17:
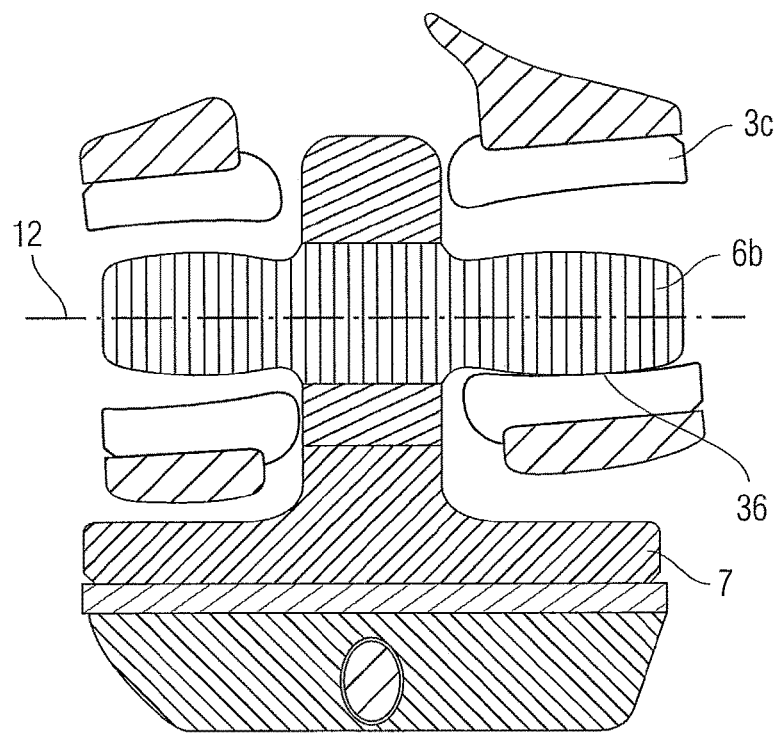
Figure 18:
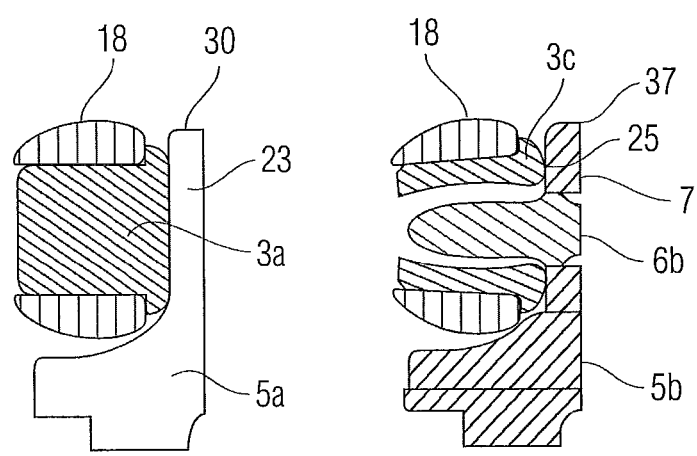

The humeral bushing 3b,c, as illustrated in FIGS. 15 and 16 to be used in the linked total elbow configuration, has a cylindrical outer diameter 24 that is press-fit into the inner diameter 17 of medial $18_M$ or lateral humeral $18_L$ condyles. In one example, the inner diameter can be conical 26a to increase contact area when it contacts the end 34a of a conical-shaped axle 6a. The cone angle of the conical axle 6a is less than the cone angle of the inner diameter 26a of conical bushing 3b. In another example, the articulation 36 between the barrel-shaped bushing 3c and the barrel-shaped axle 6b is non-conforming. This curved articulation allows for improved contact pressure at all ranges of motion where axle 6b contacts bushing 3c as illustrated in FIG. 17. The bushing's central face 25 articulates with post 37 of the linked ulnar bearing housing during medial-lateral translation, as illustrated in FIG. 18. The bushing may be made of a low friction material, for example, ultra-high molecular weight polyethylene (UHMWPE).

Humeral Bushing Cap for Unlinked Configuration

The humeral bushing hole cap 3a, as illustrated in FIG. 15, can be inserted into the cylindrical hole 17 of either the medial $18_M$ or lateral $18_L$ humeral condyle, and can be used in an unlinked total elbow configuration. The central face 23 of the cap articulates with the post 30 of the unlinked ulnar bearing 5a during medial-lateral translation, as illustrated in FIG. 18. Should the elbow be converted to a linked configuration, the caps 3a can be removed and discarded.

Figure 19:
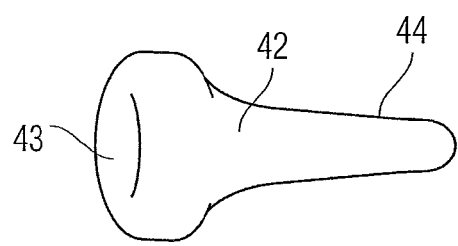

A radial head component 42, as illustrated in FIG. 19, has a proximal body 43 that articulates with the capitellum. The component 42 has a distal stem 44 that follows the axis of the shaft of the radius. The stem 44 is coated with plasma spray or provided with porous metal by additive manufacturing and possibly hydroxyapatite to promote cementless fixation to bone.

A preferred overall carrying angle of the elbow replacement device is 10° where the ulna has 3° of carrying angle, and the humerus has °.

The range of motion of the device may be from 0-160° degrees of flexion.

The device can be imbedded with a material that resorbs over time in parallel with the time it takes for the native elbow soft tissue structures to heal. As the native elbow strengthens during the healing process, the resorption of the material causes the joint of the elbow replacement to become less stiff.

With regard to the unlinked design, the convex humeral condyles 18 articulate with a concave unlinked ulnar bearing surface 31. The articulation-adjustable ulnar stem 4 is allows for ulnar bearing 5a exchange if the component wears or if a different constraint type is needed. The ulnar bearing 5a can come in various thicknesses y to provide intra-operative adjustment of soft tissue constraint. The post 37 can come in various thicknesses δ to provide intra-operative adjustment of implant constraint. The ulnar bearing 5a is assembled to the ulnar stem 4 from approximately a medial and/or lateral direction in order to preserve the triceps attachment to the proximal ulna. Should the humeral component not have a modular condyle connection 19a and 19b, the bushings holes 17 can be capped-off 3a to allow the condyles 18 and the bushing cap central face 23 to articulate with the unlinked ulnar bearing 5a.

With regard to the linked design, each convex humeral component condyle 18 has cylindrical holes 17 along the same axis that capture press-fit humeral bushings 3b,c. The linked ulnar bearing housing 7 is assembled to ulnar stem 4 from approximately a medial and/or lateral direction by means of a sliding capture mechanism 28 to preserve the triceps attachment to the proximal ulna. The linked, convex ulnar bearing 5b engages with the ulnar bearing housing 7 and can be revised if, for example, the bearing surface wears over time. The axle 6 rigidly locks to the ulnar bearing housing 7 using, for example, a locking component 9. The humeral articular surfaces engage the ulnar articular surfaces in sequence (FIGS. 17 and 18): 1. Upon varus/valgus rotation, the medial and/or lateral humeral condylar surfaces $21_{M,L}$ articulate with the medial and/or lateral bearing surfaces 41 of the linked ulnar bearing, respectively. 2. With further rotation, lift-off of one humeral condyle from one ulnar bearing surface occurs, and the axle 6 articulates with the inner surfaces 26 of the humeral bushings 3b,c. 3. Upon further rotation and medial-lateral translation, the central faces 25 of the humeral bushings 3b,c articulate with the post 37 of the linked ulnar bearing housing.

Total Elbow Replacement Device

Figure 23:
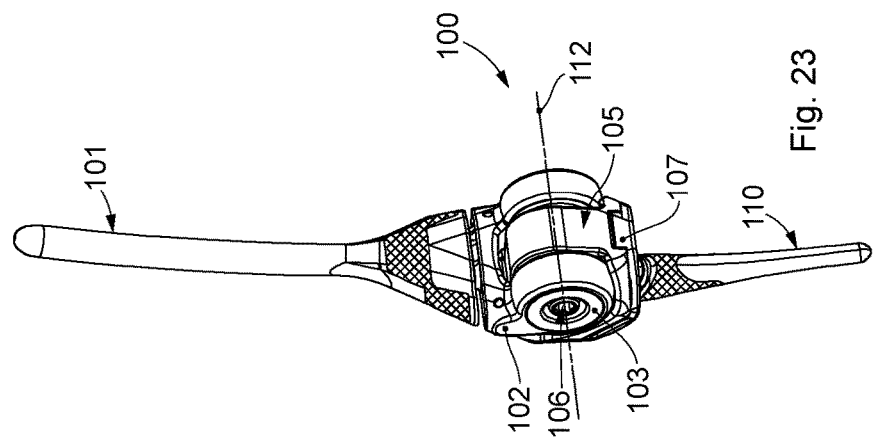
FIG. 23 provides a perspective view of an illustrative modular, linked elbow replacement device in accordance with some embodiments of the disclosed subject matter.

FIGS. 20 to 33 are used to describe embodiments, combinable with all embodiments described herein, of a total elbow replacement device 100 according to the present disclosure. The total elbow replacement device 100 is developed to be used for total replacements and to allow a surgeon to intraoperatively select an unlinked or a linked constraint, by simply adding/removing a hinging pin or axle 106. See for instance FIG. 23, which is used to describe a modular, linked elbow replacement device 100 in accordance with embodiments of the present disclosure.

According to embodiments, the hinging axle 106 can include a threaded and tapered, or conical shaped, mid-portion 106a (see e.g. FIGS. 20, 22, 24 and 25).

According to embodiments, combinable with all embodiments described herein, the total elbow replacement device 100 basically includes two main parts, i.e. a humeral component, or humeral implant, 119 and an ulnar component, or ulnar implant, 104. The humeral component 119 and the ulnar component 104 are configured to articulate with each other around an articulation axis. In the case of linked constraint configuration, the two parts, humeral component 119 and the ulnar component 104, can be mechanically hinged to each other around a hinging axis 112, which coincides in this case with the above mentioned articulation axis, by inserting, mating and screwing the above mentioned hinging axle 106, which can be, for instance, a metal axle. The hinging axle 106 can be mated and screwed to the ulnar component 104 by the threaded and tapered, or conical shaped, mid-portion 106a. For changing from linked to unlinked constraint configuration, it is sufficient to remove the hinging axle 106, e.g. by unscrewing and decoupling. In the unlinked configuration, where the hinging axle 106 is removed, no mechanical hinging constraint is provided, nevertheless the humeral component 119 and the ulnar component 104 can in any case articulate each other around the articulation axis.

According to embodiments, combinable with all embodiments described herein, the humeral component 119 can include a humeral stem 101, a humeral condyle body 102 and two humeral bushings 103.

The condyle body 102 can be connected to the distal end of the humeral stem 101. In accordance with possible implementations, humeral stem 101 and humeral condyle body 102 can be connected in a releasable manner, i.e. connection of the condyle body 102 to the distal end of the humeral stem 101 can be of the removable type, thereby establishing modularity in both linked and unlinked elbow systems. The condyle body 102 can be connected to the distal end of the humeral stem 101 by mechanical connection, e.g. a taper connection. Taper connections as used in association with the embodiments described herein may refer for instance to standardized tapered shapes, essentially defined by slopes cut in a rod.

In possible implementations, a humeral screw 108 can be provided to connect the condyle body 102 and the humeral stem 101. The humeral screw 108 can be used to safely connect the condyle body 102 and the humeral stem 101. For instance, the humeral screw 108 can connect the condyle body 102 and the humeral stem 101 through the above mentioned mechanical connection, e.g. the taper connection.

In possible implementations the condyle body 102 can be provided with a bicondylar portion, in particular comprising distally extending and spaced apart condyle portions, or condyles, 118 (i.e. medial and lateral condyles). The condyle portions 118 are spaced apart each other to receive a portion of the ulnar component 104, as described below in more detail. Furthermore, the condyle portions 118 are configured to articulate with mating articulation housings 139 provided in the ulnar component 104 during medial-lateral translation, as described below in more detail. In particular, the condyle portions 118 are configured to define condyle bearing surfaces 121.

According to embodiments, each of the two spaced apart humeral condyle portions 118 is provided with inner articulation annular walls 115, defining central faces 116 of the humeral condyle portions 118. The annular walls 115 radially inwards project from the inner peripheral edges of the condyle portions 118. The annular walls 115 can be for instance defined by annular bands or a ring-shaped structure, such as a radial annular or rimmed prominence or appendage. In possible implementations, the annular walls 115 can be bulged or convex and, moreover, their peripheral edge can be chamfered or rounded.

According to embodiments, combinable with all embodiments described herein, the two humeral bushings 103 can be inserted into the humeral condyle body 102, in particular into the condyle portions 118.

According to embodiments, combinable with all embodiments described herein, the two humeral bushings 103 and the humeral condyle body 102 can be configured for reciprocal connection and stable positioning by mechanical interference. In particular, according to possible implementations, the two humeral bushings 103 and the humeral condyle body 102, in particular the condyle portions 118, can be provided with mating male and female cylindrical portions for reciprocal mechanical connection with interference (i.e. press-fit), to provide the above mentioned reciprocal connection and stable positioning. In particular, the connection humeral bushings 103 and the humeral condyle body 102, in particular the condyle portions 118, can be connected by interference between the male and female cylindrical portions present in the components involved.

According to embodiments, combinable with all embodiments described herein, the two humeral bushings 103 can be inserted into the condyle portions 118 of the humeral condyle body 102, to define a specific articulation geometry and to allow the insertion of the hinging axle 106, in case of a linked configuration.

In possible implementations, the humeral condyle body 102 can be provided with bushing holes 117. Specifically, each of the condyle portions 118 of the humeral condyle body 102 can be provided with a bushing hole 117. The bushing holes 117 can each be configured to receive and stably position the respective humeral bushings 103. For example, the bushing holes 117 can be sized to mate with the humeral bushings 103. In particular, the humeral bushings 103 can be press-fitted into the bushing holes 117. The bushing holes 117 can be aligned along the above mentioned hinging axis 112. The bushing holes 117 are made as holes passing through the condyle portions 118 along the hinging axis 112 and are delimited, on the inner side of the condyle body 102, by the above mentioned articulation annular walls 115. The articulation annular walls 115 project radially, circumferentially surrounding, the bushing holes 117 on the inner side of the condyle portions 118, thereby narrowing the diameter of the bushing holes 117, in order to axially block the humeral bushing 103 received in the respective bushing hole 117, while, on the outer side of the condyle portions 118, the diameter of the bushing holes 117 is not reduced, i.e. it is larger, in order to allow insertion of the humeral bushing 103 along the hinging axis 112. Due to the provision of the articulation annular walls 115, the humeral bushings 103 can be inserted into the bushing holes 117 from outside the condyle portions 118, along the hinging axis 112.

The humeral bushings 103 can be retained inside the respective bushing holes 117 by mechanical interference, in particular cylindrical interference, across the whole length of the bushing holes 117. In particular, each of the humeral bushings 103 can have a cylindrical outer diameter to press-fit into an inner diameter of bushing holes 117 of humeral condyle portions 118.

Moreover, the articulation annular walls 115 provided internally between the two condyle portions 118 also define suitable articulation surfaces, i.e. the above mentioned central faces 116, to articulate with central covering fin 130 of ulnar bearing 105, as below described in greater details.

Figure 22:
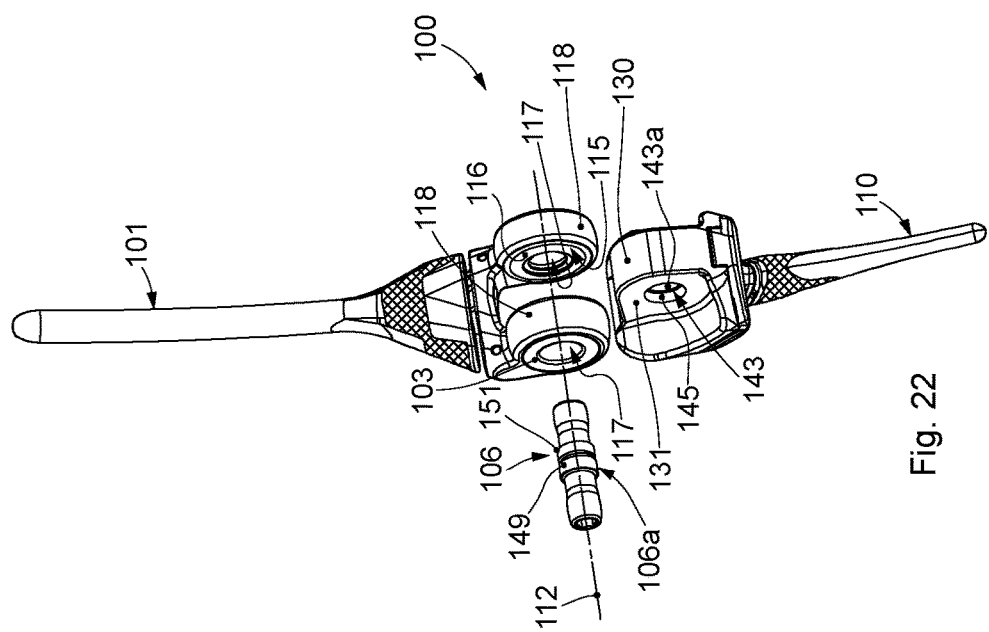
FIG. 22 provides a perspective view of an illustrative modular elbow replacement device in accordance with some embodiments of the disclosed subject matter.
Figure 27:
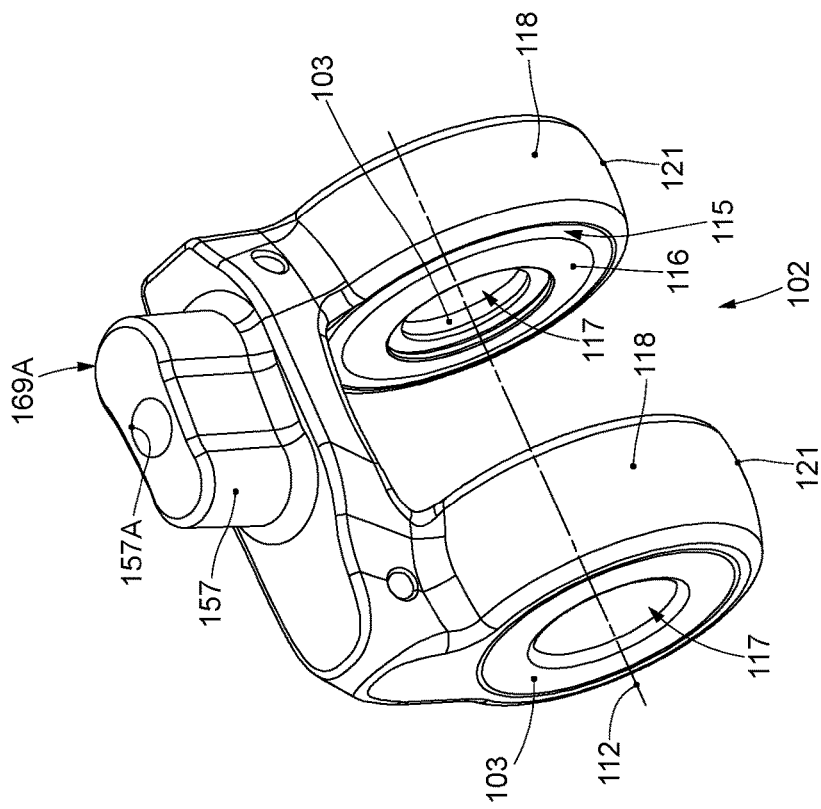
FIG. 27 provides a perspective view of a humeral condyle body of a modular elbow replacement device in accordance with some embodiments of the disclosed subject matter.
Figure 26:
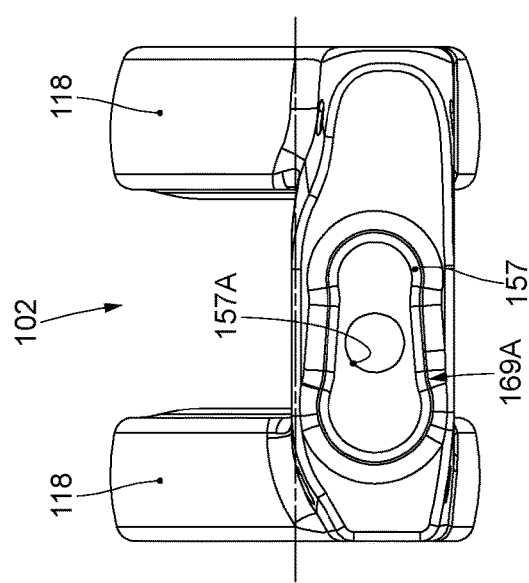
FIG. 26 provides a top plan view of a humeral condyle body of a modular elbow replacement device in accordance with some embodiments of the disclosed subject matter.
Figure 29:
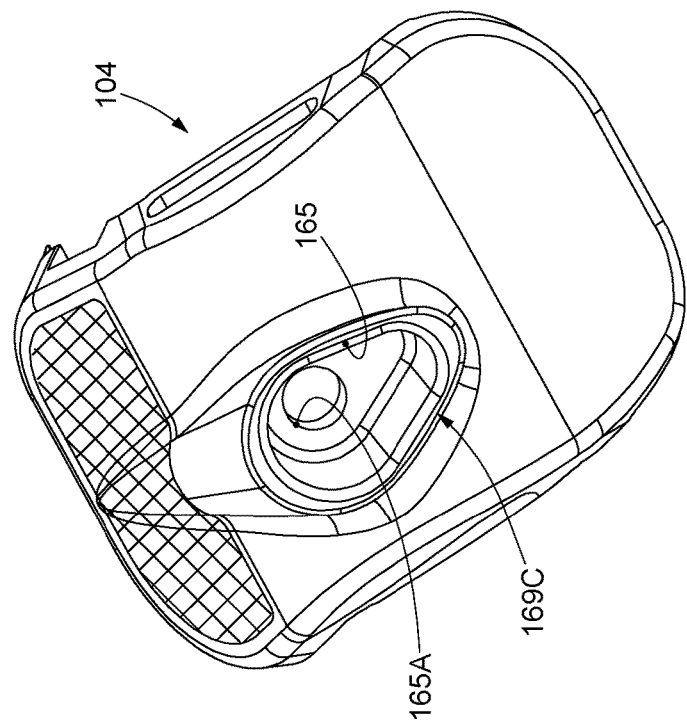
FIG. 29 provides a perspective view of an ulnar body of a modular elbow replacement device in accordance with some embodiments of the disclosed subject matter.
Figure 28:
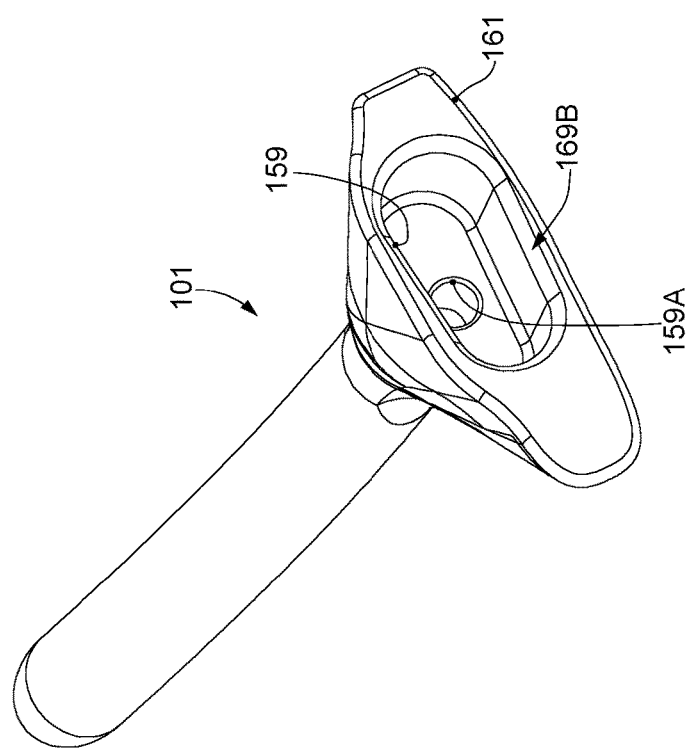
FIG. 28 provides a top plan view of a humeral stem of a modular elbow replacement device in accordance with some embodiments of the disclosed subject matter.
Figure 31:
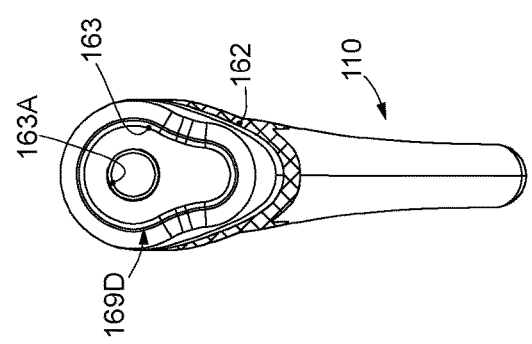
FIG. 31 provides a top plan view of an ulnar stem of a modular elbow replacement device in accordance with some embodiments of the disclosed subject matter.
Figure 30:
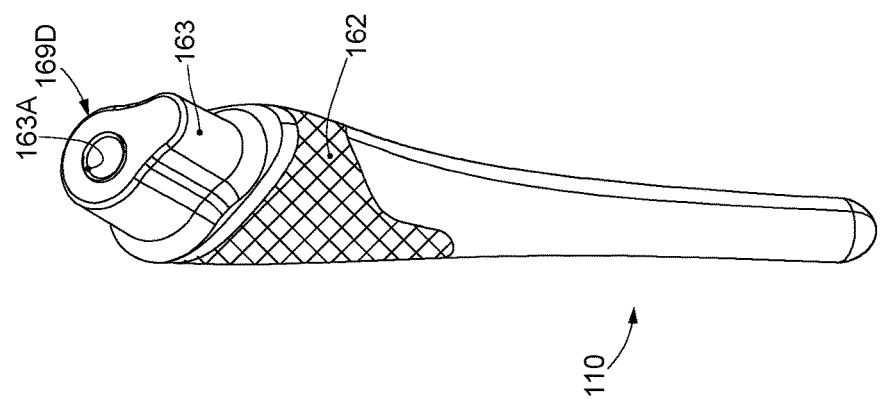
FIG. 30 provides a perspective view of an ulnar stem of a modular elbow replacement device in accordance with some embodiments of the disclosed subject matter.
Figure 33:
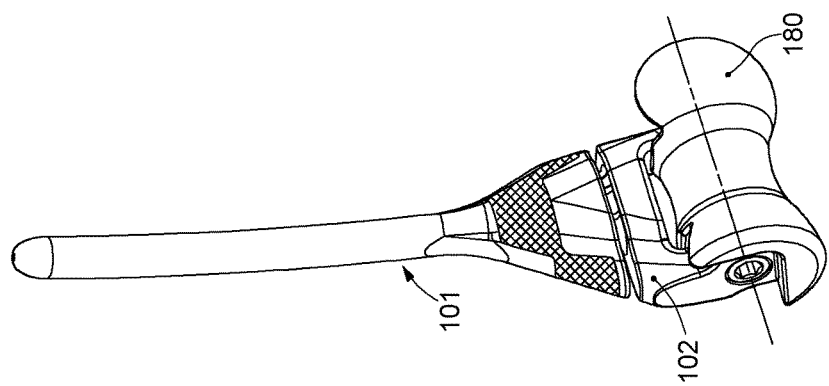
FIG. 33 provides a perspective view of an illustrative spool anatomic prosthetic system obtainable by a modular elbow replacement device in accordance with some embodiments of the disclosed subject matter.
Figure 32:
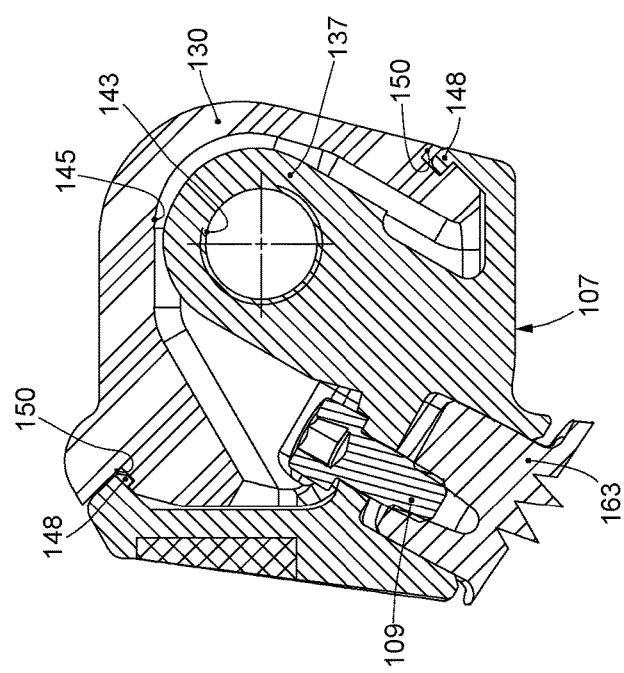
FIG. 32 provides a crosswise section of an illustrative modular elbow replacement device in accordance with some embodiments of the disclosed subject matter.

The above hinging axle 106 can be disposed along the hinging axis 112, through the bushing holes 117 of the condyle portions 118 and the humeral bushings 103 (see for instance FIG. 22). In this way, the total elbow replacement device 100 described herein can be configured with a linked constraint (see e.g. FIG. 23). By removing the hinging axle 106, the total elbow replacement device 100 described herein can be configured with an unlinked constraint.

In accordance with possible advantageous embodiments described using FIGS. 20 to 32, there is no need to provide different types of humeral bushings when intraoperatively switching from one to the other configuration.

According to embodiments, combinable with all embodiments described herein, the humeral stem 101, the humeral condyle body 102, in particular the humeral condyle portions 118, the hinging axle 106 and the humeral screw 108, can be made of metal, in particular biocompatible metal. One example of metal can be titanium or titanium-based alloy.

According to embodiments, combinable with all embodiments described herein, the two humeral bushings 103 can be made of low friction material, in particular plastic polymer, more in particular biocompatible plastic polymer. One example of plastic polymer may be polyethylene or polyethylene-based polymer. One specific example can be ultra-high molecular weight polyethylene (UHMWPE).

According to embodiments, combinable with all embodiments described herein, the ulnar component 104 can include an ulnar stem 110, a proximal ulnar body, or ulnar housing, 107 and an ulnar bearing 105. The ulnar body 107 and the ulnar bearing 105 can be configured for reciprocal coupling in a coupled condition. Moreover, the ulnar bearing 105 and the condyle portions 118 of the humeral component 119 are configured for reciprocal articulation about the hinging axis 112 in an articulation condition.

The ulnar body 107 can be connected to the ulnar stem 110. In accordance with possible implementations, ulnar stem 110 and ulnar body 107 can be connected in a releasable manner, i.e. connection of the ulnar body 107 to the ulnar stem 110 can be of the removable type, thereby establishing modularity in both linked and unlinked elbow systems. According to embodiments, the proximal ulnar body 107 can be connected to the ulnar stem 110 by mechanical connection, e.g. a taper connection.

In possible implementations, an ulnar screw 109 can be provided to connect the proximal ulnar body 107 and the ulnar stem 110. The ulnar screw 109 can be used to safely connect the proximal ulnar body 107 and the ulnar stem 110. For instance, the ulnar screw 109 can connect the proximal ulnar body 107 and the ulnar stem 110 through the above mentioned mechanical connection, e.g. the taper connection.

According to embodiments, the proximal ulnar body 107 can be connected to the ulnar bearing 105 by mechanical connection, e.g. by a snap-fit locking mechanism.

According to embodiments, the ulnar bearing 105 can be provided with a central covering fin 130, defining, on opposite sides, two respective articulation housings 139 for receiving and articulating with the above mentioned humeral condyle body 102, in particular the two spaced apart humeral condyle portions 118. Moreover, the humeral portion's central faces 116 of the articulation annular walls 115 articulate with lateral surfaces 131 of the central covering fin 130 of the ulnar bearing 105 during medial-lateral translation.

Advantageously, in the embodiments in which the humeral condyle portions 118 are made of metal and the ulnar bearing 105 is made of low-friction material as described hereinbelow in greater detail, the humeral portion's central faces 116 of the articulation annular walls 115 of the humeral condyle portions 118 result also to be made of metal and can articulate with the central covering fin 130 which result also to be made of low-friction material. Articulation between components or surfaces made respectively of metal and low-friction material may be desirable in the context of elbow replacement prosthesis according to the present disclosure, in order to improve articulation and reduce wear of articulating parts.

According to embodiments, the proximal ulnar body 107 can be provided with a central fin, or post, 137. The central fin 137 is configured for coupling with the ulnar bearing 105. In particular, the ulnar bearing 105 is provided with a coupling slot 141 (see e.g. FIGS. 24 and 25), configured to receive the above mentioned central fin 137. In particular, the coupling slot 141 is provided in the central covering fin 130 of the ulnar bearing 105. The ulnar bearing 105 is disposed over the central fin 137, which is thus inserted into the coupling slot 141 of the ulnar covering post 130, so that the central covering fin 130 covers or embeds the central fin 137. The central fin 137 can thus be completely contained in the bulk of the ulnar covering post 130. The central fin 137 can be advantageous for decreasing bending stresses on the ulnar bearing 105, for instance in the unlinked configuration.

According to possible implementations, the central fin 137 can be provided with an ulnar coupling hole, or opening, 143. In this way, the central fin 137 can allow insertion of the hinging axle 106 for the linked configuration.

According to embodiments, the hinging axle 106 can be fixedly attachable to the ulnar coupling hole 143. In possible implementations, the ulnar coupling hole 143 can be provided with a threaded and tapered, or conical shaped, portion 143a (see e.g. FIGS. 20, 22, 24 and 25) mating with the above cited threaded and tapered, or conical shaped, mid-portion 106a of the hinging axle 106, for mating and screwing to said hinging axle 106. The provision of the mating obtained by the tapered or conical shaped portions together with the screwing of the threaded portions of the hinging axle 106 and the ulnar coupling hole 143 is advantageous because it strengthens and renders stable and reliable the coupling between hinging axle 106 and ulnar coupling hole 143, which otherwise may tend to unscrew and loosen in the case that they were only screwed together.

In particular, the hinging axle 106 can be mated and screwed to the central fin 137 by the ulnar coupling hole 143. The ulnar bearing 105 can likewise be provided with an ulnar hinging hole, or opening, 145, which is axially aligned, when the ulnar bearing 105 is coupled to the proximal ulnar body 107, with the ulnar coupling hole 143. The ulnar hinging hole 145 and the ulnar coupling hole 143 are through hole made respectively through the ulnar bearing 105 and the ulnar body 107 to allow complete through passage of the hinging axle 106 along the hinging axis 112.

According to possible implementations, the threaded and tapered, or conical shaped, portion 143a of the ulnar coupling hole 143 can be provided with a inner threaded surface 147 and, for instance, with a taper connection surface 149, e.g. a taper connection (see e.g. FIG. 25). Accordingly, the above mentioned threaded and tapered, or conical shaped, mid-portion 106a of the hinging axle 106 can be provided with a mating threaded surface 151 and a tapered surface 152 (see FIGS. 20, 22, 24 and 25), configured to screw fit respectively with the inner threaded surface 147 and the taper connection surface 149 of the threaded and tapered, or conical shaped, portion 143a. The mating threaded surface 151 and tapered surface 152 can be, therefore, in a central portion of the hinging axle 106. The hinging axle 106 can also be provided with a barrel-shaped end portion 153 and an opposite barrel-shaped end portion 155. The barrel-shaped end portions 153, 155 are configured to articulate with inner surfaces of the above mentioned humeral bushings 103. The mating threaded surface 151 and tapered surface 152 of the hinging axle 106 can be in a central portion between the barrel-shaped end portion 153 and the opposite end portion 155. The end portion 153 can have a narrower cross-section diameter with respect to the cross-section diameter of the opposite end portion 155, the narrower cross-section diameter of the end portion 153 being fit for insertion through the ulnar coupling hole 143, while the cross-section diameter of the opposite end portion 155 may be oversized with respect to the diameter of the ulnar coupling hole 143. In this way it is possible to define a univocal insertion direction of the hinging axle through the ulnar coupling hole 143 along the hinging axis 112. In other embodiments, one or both of the end portions 153, 155 can be for instance cylindrical-shaped or conical-shaped. For instance, the opposite end portion 155 can be cylindrical, or axially tapered towards the middle of the hinging axle 106.

The hinging axle 106 can also be provided with a polygonal, e.g. hexagonal, hollow head, for instance provided at the end portion 153 or, alternatively, at the opposite end portion 155, and configured for receiving a mating screwing tool, e.g. an Allen key.

According to possible implementations, the ulnar body 107 can be provided with one or more protruding attachment ridge, or tooth, 148 or similar engagement features. Accordingly, the ulnar bearing 105 can be provided with one or more mating slots 150, or similar capture mechanism, configured for engaging with a respective attachment ridge 148 of the ulnar body 107 (see for instance FIG. 32). Engagement between attachment ridge 148 and slot 150 thus can provide mechanical connection of the ulnar body 107 and the ulnar bearing 105.

According to embodiments, combinable with all embodiments described herein, the ulnar stem 110, the proximal ulnar body 107 and the ulnar screw 109 can be made of metal, in particular biocompatible metal. One example of metal may be titanium or titanium-based alloy.

According to embodiments, combinable with all embodiments described herein, the ulnar bearing 105 can be made of low friction material, in particular plastic polymer, more in particular biocompatible plastic polymer. One example of plastic polymer may be polyethylene or polyethylene-based polymer. One specific example can be ultra-high molecular weight polyethylene (UHMWPE).

According to advantageous embodiments of the present disclosure, the hinging axle 106 and the ulnar body 107 are made of metal, as above described, and therefore an appropriate mechanical resistance is achieved for the hinging of the humeral component 119 and the ulnar component 104 about the hinging axis 112 in the linked configuration. Moreover, screwed connection of the hinging axle 106 to the ulnar body 107 achieves safety and reliability of the connection between humeral component 119 and ulnar component 104.

According to advantageous embodiments of the present disclosure, the humeral bushings 103 are made of the above mentioned low friction material and this allows an appropriate articulation of the hinging axle 106 made of metal in the humeral bushings 103, both in the linked and unlinked configuration.

According to advantageous embodiments of the present disclosure, the humeral condyle body 102 is made of metal as above described and the ulnar bearing 105 is made of the above mentioned low friction material and this allows an appropriate articulation of the humeral condyle body 102 made of metal with respect to the ulnar bearing 105, both in the linked and unlinked configuration. In particular, in such embodiments the condyle bearing surfaces 121 and inner articulation annular walls 115 of the humeral condyle body 102 can be made of metal and, both in the linked and in the unlinked configuration, they respectively are in contact and articulate with the articulation housings 139 and the side faces of the central fin, or post, 137 which can be made of the above mentioned low friction material.

Embodiments described herein also refer to a method of converting an elbow prosthesis 100 that includes the humeral component 119 and the ulnar component 104 from an unlinked configuration to a linked configuration, or vice versa, while the elbow prosthesis is in situ.

In the case of conversion from an unlinked configuration to a linked configuration the method consists of:

linking the humeral component 119 and the ulnar component 104 by passing, along the hinging axis 112, the hinging axle 106 through the humeral bushings 103 of the condyle portions 118 of the humeral component 119 and through the ulnar hinging hole 145 and ulnar coupling hole 143 aligned along said hinging axis 112 and respectively formed in the ulnar bearing 105 and the ulnar body 107 that are part of the ulnar component 104, and by mating and screwing the hinging axle 106 to the ulnar coupling hole 143.

In the case of conversion from a linked configuration to an unlinked configuration the method consists of:

unlinking the humeral component 119 and the ulnar component 104 by unscrewing and decoupling the hinging axle 106 from the ulnar coupling hole 143 and by passing, along the hinging axis 112, the hinging axle 106 through the humeral bushings 103 of the condyle portions 118 of the humeral component 119 and through the ulnar hinging hole 145 and ulnar coupling hole 143 aligned along said hinging axis 112 and respectively formed in the ulnar bearing 105 and the ulnar body 107 that are part of the ulnar component 104.

According to embodiments, combinable with all embodiments described herein, the total elbow replacement 100 can be provided with modular configuration of the humeral component 119 and the ulnar component 104 and in particular by the removable connection between the humeral stem 101 and the humeral condyle body 102 and between the ulnar stem 110 and the proximal ulnar body 107. In possible implementations, the humeral stem 101 and/or the ulnar stem 110 can be provided with one or more surfaces or portions configured to promote cementless fixation to bone, i.e. to promote osteointegration. According to specific implementations, such one or more surfaces or portions configured to promote cementless fixation to bone are provided only on the humeral stem 101 and/or the ulnar stem 110, and not on the condyle body 102 and/or the ulnar body 107.

According to embodiments, combinable with all embodiments described herein, the humeral condyle body 102 can be provided with a humeral extending body 157 mating with a humeral seat 159 (see for instance FIG. 28) provided in an end portion 161 of the humeral stem 101, thereby establishing modularity in both linked and unlinked elbow systems for the humeral component 119. The end portion 161 of the humeral stem 101 can be configured to promote cementless fixation to bone, i.e. to promote osteointegration. In particular, in possible implementations, an outer surface of the end portion 161 of the humeral stem 101 may be coated with plasma spray or may include porous metal provided by additive manufacturing and possibly hydroxyapatite. In specific implementations, the end portion 161 of the humeral stem 101 may be provided at least in part with a trabecular structure, such as a titanium-based (e.g. titanium alloy $Ti_6Al_4V$) or a cobalt alloy-based trabecular structure, to promote osteointegration.

For example, according to possible embodiments, a trabecular structure can be defined by a lattice structure with cells defining a plurality of cavities disposed three-dimensionally, open and inter-communicating, connected with each other. In particular, the lattice structure can be formed, without a break in continuity, by one or more models of a plurality of geometric meshes that are repeated in space, having a cellular geometry with elementary cells open and contiguous, so as to define a plurality of polygons, e.g. hexagons, with a spatial development delimiting the cavities, so that the lattice is able to promote osteo-integration. In possible implementations, each geometric mesh may have a polygonal, e.g. hexagonal, shape with vertexes that are not co-planar and the open free area of each elementary cell may have an equivalence to a circle with an equivalent diameter comprised in a range from about 0.3 mm to about 1.5 mm.

According to the present disclosure, a trabecular structure that can be used with the embodiments described herein can be obtained for instance by a wide range of techniques, from synthesis to additive manufacturing (AM), including DMSLS (Direct Metal Selective Laser Sintering), SLM (Selective Laser Melting), EBM (Electron Beam Melting), to conventional machining, where applicable.

According to embodiments, combinable with all embodiments described herein, the ulnar stem 110 can be provided with an end portion 162 having an ulnar extending body 163 mating with an ulnar seat 165 (see for instance FIG. 29) provided in the ulnar body 107, thereby establishing modularity in both linked and unlinked elbow systems also for the ulnar component 104. The end portion 162 of the ulnar stem 110 can be configured to promote cementless fixation to bone, i.e. to promote osteointegration. In particular, in possible implementations, an outer surface of the end portion 162 of the ulnar stem 110 may be coated with plasma spray or may include porous metal provided by additive manufacturing and possibly hydroxyapatite. In specific implementations, the end portion 162 of the ulnar stem 110 may be provided at least in part with a trabecular structure, such as a titanium-based (e.g. titanium alloy $Ti_6Al_4V$) or a cobalt alloy-based trabecular structure, to promote osteointegration.

According to embodiments, combinable with all embodiments described herein, the humeral extending body 157 and the mating humeral seat 159, as well as the ulnar extending body 163 and the mating ulnar seat 165 are provided with respective holes 157A, 159A, 163A and 165A for inserting the above mentioned humeral screw 108 and ulnar screw 109, respectively (see e.g. FIGS. 26, 27, 28, 29, 30 and 31).

According to embodiments, combinable with all embodiments described herein, the humeral extending body 157 and the mating humeral seat 159, as well as the ulnar extending body 163 and the mating ulnar seat 165, may be configured, in particular shaped, to define a reciprocal geometric coupling, more specifically a conical coupling, for instance a taper connection as above disclosed.

According to embodiments, combinable with all embodiments described herein, the humeral extending body 157 and the mating humeral seat 159, as well as the ulnar extending body 163 and the mating ulnar seat 165 can be provided with one or more reliefs or undercuts and can also be provided with an asymmetric double-curved shape. This asymmetric double curved-shape can be effective for anti-rotation of the coupled components, i.e. humeral stem 101 and humeral body 102 and ulnar stem 110 and ulnar body 107. In particular, such shape may be for instance delimited by an asymmetric double-curved outer peripheral profile 169A, 169B, 169C and 169D (see e.g. FIGS. 26, 27, 28, 29, 30 and 31). In possible implementations, this peripheral profile 169A, 169B, 169C and 169D may be defined by two spaced circumferences with different diameters, i.e. one circumference with a long diameter and another circumference with a short diameter. Moreover, the two circumferences can be joined by a joining surface profile, for instance having converging segments, such as linear or curved segments. This asymmetric double curved-shape in the peripheral profiles 169A and 169D of the humeral extending body 157 and the ulnar extending body 163 can be provided with reliefs or undercuts in the surface joining the two circumferences. One advantage of this shape configuration may be that it is thus guaranteed a reliable contact of the humeral seat 159 and the ulnar seat 165 on the surfaces of the two circumferences of the humeral extending body 157 and the ulnar extending body 163, where the profile can be controlled in an effective manner. One further advantage of the provision of reliefs or undercuts on the peripheral profiles 169A and 169D of the humeral extending body 157 and the ulnar extending body 163 may be that reduced contact surfaces can be achieved and this may result in a reduced development of particulate caused by fretting. For example, the two circumferences of the peripheral profiles 169A and 169D of the humeral extending body 157 and the ulnar extending body 163 can be joined by converging segments, such as linear or curved segments, that may be shaped to define the above cited reliefs or undercuts. This shape may provide the advantage of optimizing resistance to mechanical stresses during use.

According to embodiments, combinable with all embodiments described herein, general modularity of the components of the total elbow replacement 100 can be provided by the modular configuration of the humeral component 119 and the ulnar component 104 and in particular by the removable connection between the humeral stem 101 and the humeral condyle body 102 and between the ulnar stem 110 and the proximal ulnar body 107. This modularity allows the selection of different kind of humeral and/or ulnar stems, e.g. cemented, non-cemented/cementless or revision and different distal humeral parts, e.g. anatomic spool 180 (such as for hemi prosthetic system, see e.g. FIG. 33) or humeral condyle body 102 and make it easier the operation steps in case of revision surgical operation.

The surgical technique for implanting in a patient the elbow replacement device disclosed herein avoids taking down the triceps. A medial or lateral approach can be used to implant the device. The approach is not minimally invasive, but rather soft tissue preserving. The lateral soft tissue structures are preserved. The distal humeral epicondyles can be retained. Resection of the radial head is optional.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A modular elbow prosthesis comprising:
   a humeral component (119) comprising a humeral stem (101) and a humeral condyle body (102) detachably connected to the humeral stem (101), the humeral condyle body (102) comprising two distally extending condyle portions (118) each having a condylar bearing surface (121), a bushing hole (117) extending through the condyle portion (118), and a humeral bushing (103) retained inside the bushing hole (117), the humeral bushings (103) configured to receive a hinging axle (106) along a hinging axis (112);
   an ulnar component (104) comprising an ulnar stem (110), ulnar body (107) detachably connected to the ulnar stem (110), and an ulnar bearing (105) detachably coupled to the ulnar body (107), the ulnar body (107) comprising a central fin (137) provided with an ulnar coupling hole (143), the ulnar bearing (105) comprising a central covering fin (130) provided, on opposite sides of the central covering fin (130), with two respective articulation housings (139) defining complementary bearing surfaces that receive and articulate with the condylar bearing surfaces (121) of the humeral condyle portions (118); and
   a hinging axle (106) comprising a barrel-shaped end portion (153), an opposite barrel-shaped end portion (155), and a threaded and tapered, or conical shaped, midportion (106a) extending between the barrel-shaped end portions (153, 155);
   wherein the condyle portions (118) and the ulnar bearing (105) being configured for reciprocal articulation about the hinging axis (112) in an articulation condition;
   wherein the central covering fin (130) of the ulnar bearing (105) comprises a coupling slot (141) configured to receive the central fin (137) of the ulnar body (107);
   wherein the central covering fin (130) of the ulnar bearing (105) comprises an ulnar hinging hole (145), which is axially aligned, when the ulnar bearing (105) is coupled to the ulnar body (107), with the ulnar coupling hole (143);
   wherein the hinging axle (106) passes through the humeral bushings (103), through the ulnar hinging hole (145), and through the ulnar coupling hole (143), and
   wherein the mid-portion (106a) of the hinging axle (106) is fixedly attachable to said ulnar coupling hole (143);
   wherein said ulnar coupling hole (143) is provided with a threaded and tapered, or conical shaped, portion (143a) mating with said threaded and tapered, or conical shaped, mid-portion (106a) of said hinging axle (106);
   wherein the threaded and tapered, or conical shaped, portion (143a) of the ulnar coupling hole (143) comprises a inner threaded surface (147) and a taper connection surface (149),
   and the threaded and tapered, or conical shaped, midportion (106a) of the hinging axle (106) comprises a mating threaded surface (151) and a tapered surface (152) configured to screw fit respectively with the inner threaded surface (147) and the taper connection surface (149).

2. The elbow prosthesis according to claim 1, wherein the ulnar body (107) is releasably connectable to the ulnar stem (110) by mechanical connection.

3. The elbow prosthesis according to claim 2, wherein said mechanical connection is a taper connection.

4. The elbow prosthesis according to claim 1, said prosthesis comprising an ulnar screw (109) to connect the ulnar body (107) and the ulnar stem (110).

5. The elbow prosthesis according to claim 4, wherein the ulnar screw (109) is made of metal.

6. The elbow prosthesis according to claim 1, wherein the ulnar body (107) and the ulnar stem (110) are made of metal.

7. The elbow prosthesis according to claim 1, wherein the humeral stem (101) and/or the ulnar stem (110) are provided with one or more surfaces or portions configured to promote cementless fixation to bone.

8. The elbow prosthesis according to claim 1, wherein the ulnar stem (110) is provided with an end portion (162) having an ulnar extending body (163) mating with an ulnar seat (165) provided in the ulnar body (107).

9. The elbow prosthesis according to claim 8, wherein said ulnar extending body (163) and said ulnar seat (165) are configured to define a reciprocal geometric coupling.

10. The elbow prosthesis according to claim 8, said prosthesis comprising an ulnar screw (109) to connect the ulnar body (107) and the ulnar stem (110), wherein said ulnar extending body (163) and said ulnar seat (165) are provided with respective holes (163A, 165A) for inserting said ulnar screw (109).

11. The elbow prosthesis according to claim 8, wherein said ulnar extending body (163) and said ulnar seat (165) are provided each with an asymmetric double-curved shape.

12. The elbow prosthesis according to claim 11, wherein said asymmetric double-curved shape is delimited by an asymmetric double-curved outer peripheral profile (169C, 169D).

13. The elbow prosthesis according to claim 12, wherein said peripheral profile (169C, 169D) is defined by two spaced circumferences with different diameters, joined by a joining surface profile.

14. The elbow prosthesis according to claim 8, wherein the end portion (162) of the ulnar stem (110) is configured to promote cementless fixation to bone.

15. The elbow prosthesis according to claim 14, wherein an outer surface of the end portion (162) of the ulnar stem (110) is coated with plasma spray or provided with porous metal by additive manufacturing.

16. The elbow prosthesis according to claim 14, wherein, the end portion (162) of the ulnar stem (110) is provided at least in part with a trabecular structure.

17. The elbow prosthesis according to claim 1, wherein the humeral condyle body (102) is detachably connectable to the humeral stem (101), thereby establishing modularity of both the humeral component (119) and the ulnar component (104).

18. The elbow prosthesis according to claim 17, wherein the condyle body (102) is detachably connectable to the humeral stem (101) by mechanical connection.

19. The elbow prosthesis according to claim 18, wherein said mechanical connection is a taper connection.

20. The elbow prosthesis according to claim 17, said prosthesis comprising a humeral screw (108) to connect the condyle body (102) and the humeral stem (101).

21. The elbow prosthesis according to claim 20, wherein the humeral screw (108) is made of metal.

22. The elbow prosthesis according to claim 17, wherein the humeral condyle body (102) is provided with a humeral extending body (157) mating with a humeral seat (159) provided in an end portion (161) of the humeral stem (101).

23. The elbow prosthesis according to claim 22, wherein the end portion (161) of the humeral stem (101) is configured to promote cementless fixation to bone.

24. The elbow prosthesis according to claim 23, wherein an outer surface of the end portion (161) of the humeral stem (101) is coated with plasma spray or provided with porous metal by additive manufacturing.

25. The elbow prosthesis according to claim 23, wherein the end portion (161) of the humeral stem (101) is provided at least in part with a trabecular structure.

26. The elbow prosthesis according to claim 22, wherein said humeral extending body (157) and said humeral seat (159) are configured to define a reciprocal geometric coupling.

27. The elbow prosthesis according to claim 22, said prosthesis comprising a humeral screw (108) to connect the condyle body (102) and the humeral stem (101), wherein said humeral extending body (157) and said humeral seat (159) are provided with respective holes (157A, 159A) for inserting said humeral screw (108).

28. The elbow prosthesis according to claim 22, wherein said humeral extending body (157) and said humeral seat (159) are provided each with an asymmetric double-curved shape.

29. The elbow prosthesis according to claim 28, wherein said asymmetric double-curved shape is delimited by an asymmetric double-curved outer peripheral profile (169A, 169B).

30. The elbow prosthesis according to claim 29, wherein said peripheral profile (169A, 169B) is defined by two spaced circumferences with different diameters, joined by a joining surface profile.

31. The elbow prosthesis according to claim 1, wherein the condyle body (102) and the humeral stem (101) are made of metal.

\* \* \* \* \*